United States Patent [19]

Hofmann

[11] Patent Number: 4,564,374
[45] Date of Patent: Jan. 14, 1986

[54] DEVICE FOR INCORPORATION IN DENTAL SUCTION APPARATUSES FOR SEPARATION OF LIQUID AND SOLID COMPONENTS

[75] Inventor: Hans-Joachim Hofmann, Geradstetten, Fed. Rep. of Germany

[73] Assignee: Durr-Dental GmbH & Co. KG, Bietigheim, Fed. Rep. of Germany

[21] Appl. No.: 534,362

[22] Filed: Sep. 21, 1983

Related U.S. Application Data

[63] Continuation of Ser. No. 426,274, Jul. 27, 1982, abandoned, which is a continuation of Ser. No. 187,527, Sep. 15, 1980, abandoned, which is a continuation of Ser. No. 56,852, Jul. 12, 1979, abandoned, which is a continuation of Ser. No. 889,855, Mar. 24, 1978, abandoned.

[30] Foreign Application Priority Data

Mar. 25, 1977 [DE] Fed. Rep. of Germany ....... 2713321

[51] Int. Cl.[4] ............................................ B01B 49/12
[52] U.S. Cl. .......................................... 55/57; 55/69;
55/167; 55/169; 55/184; 55/421; 210/104; 433/92
[58] Field of Search ................... 433/92; 55/165–167, 55/169, 184, 192, 421, 432, 433, 57, 69; 210/104, 114, 115

[56] References Cited

U.S. PATENT DOCUMENTS

| | | | |
|---|---|---|---|
| 1,711,428 | 4/1929 | Schafer | 210/115 |
| 3,138,873 | 6/1964 | Bishcl | 433/92 |
| 3,305,927 | 2/1967 | Mitchell | 433/92 |
| 3,868,321 | 2/1975 | Gough | 210/115 |
| 3,870,483 | 3/1975 | Ritzler | 55/192 |
| 4,031,007 | 6/1977 | Sierra, Jr. | 210/104 |
| 4,076,606 | 7/1977 | Zimmermann | 55/421 |

*Primary Examiner*—John Adee
*Attorney, Agent, or Firm*—Robert E. Burns; Emmanuel J. Lobato; Bruce L. Adams

[57] ABSTRACT

A separator for incorporation into dental suction apparatus for separating from the suction stream liquid and solid materials coming from the mouth of a patient comprises a housing, a separation chamber in the housing, an inlet for the suction stream into the separation chamber and an outlet for cleaned suction air from the separation chamber. Below the separation chamber there is a smaller collecting chamber below which is a drainage chamber provided with a liquid-solid discharge opening. In the separation chamber there is a cyclone device into which the suction stream enters tangentially so as to provide a swirling movement. The suction air then passes up through a central opening defined by the cyclone means. Also in the separation chamber there is a rotating element in the form of a rotatable float having a stem extending up from the float and provided with vanes associated with the cyclone device so as to rotate the float. The float also controls valve means so as to drain collected liquid and any solid therein from the separation chamber into the collection chamber when a certain liquid level in the separation chamber has been reached. When the valve is opened to drain the separation chamber, an outlet valve for the collection chamber is closed so as to preserve suction. During operation of the separator, except when draining the separation chamber, the collection chamber is vented to the atmosphere. The outlet for clean air from the separation chamber is provided with a shut-off valve which closes the suction line in the event liquid in the separation chamber reaches an excessive level.

40 Claims, 19 Drawing Figures

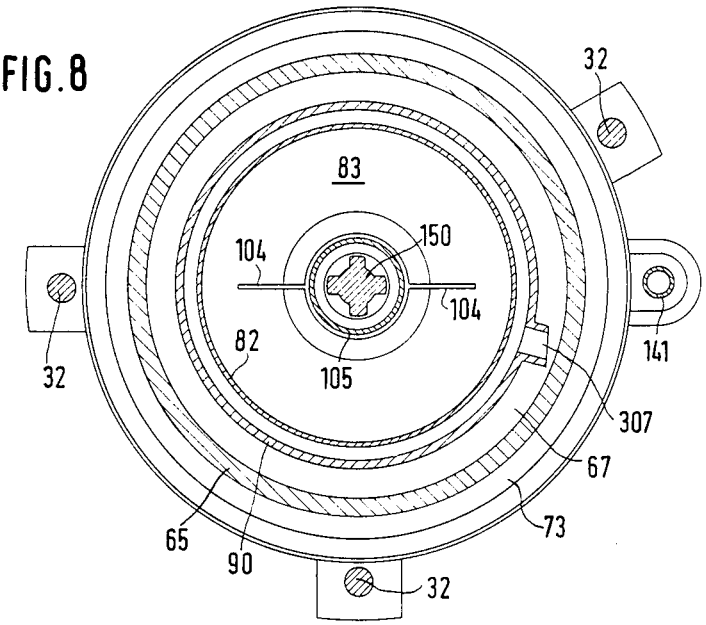
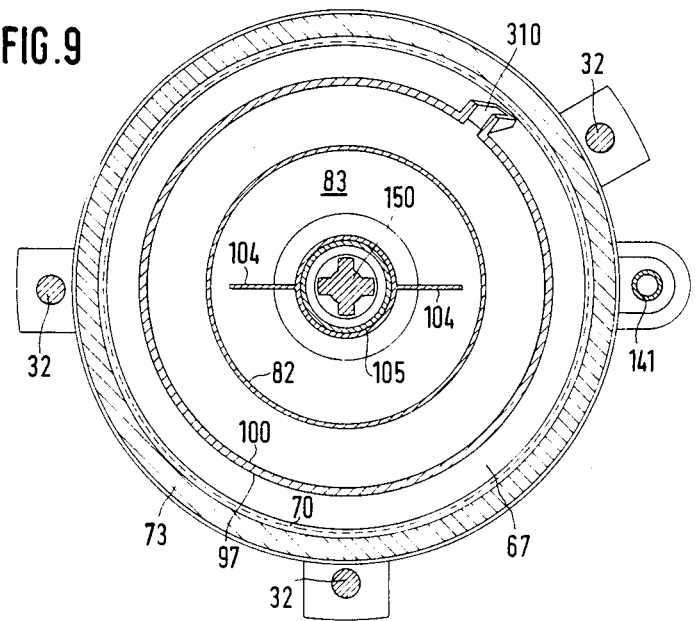

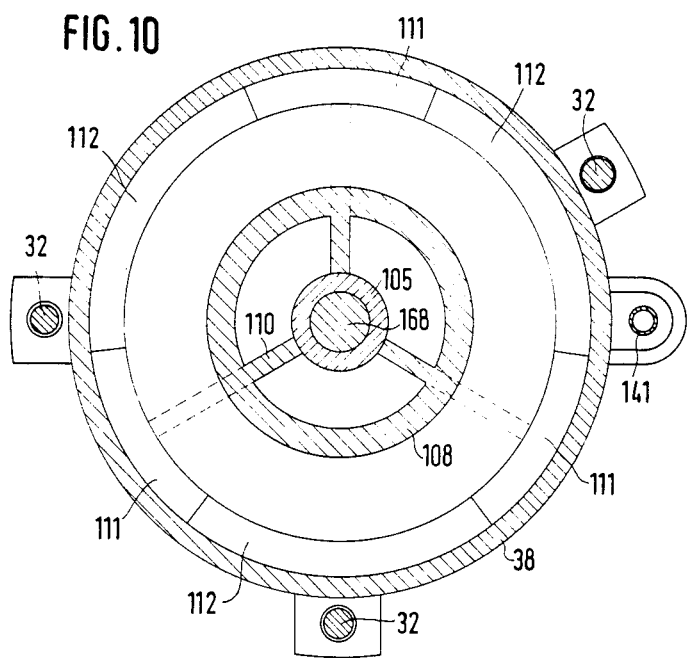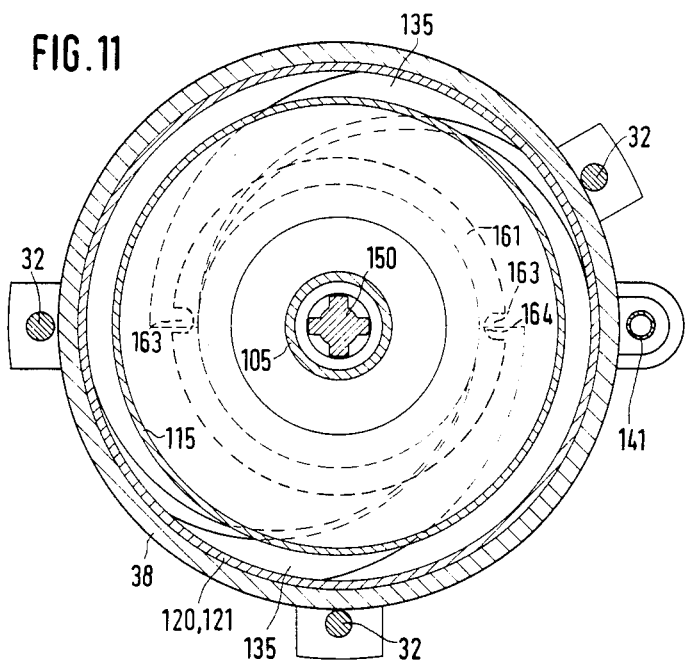

DEVICE FOR INCORPORATION IN DENTAL SUCTION APPARATUSES FOR SEPARATION OF LIQUID AND SOLID COMPONENTS

This is a continuation of application Ser. No. 426,274 filed July 27, 1982, now abandoned, which is a continuation of application Ser. No. 187,527 filed Sept. 15, 1980, now abandoned, which is a continuation of application Ser. No. 056,852 filed July 12, 1979, now abandoned, which is a continuation of application Ser. No. 889,855 filed Mar. 24, 1978 now abandoned.

The invention relates to a device for incorporation in dental suction apparatuses for separation of fluid and solid components, such as water, blood, saliva, tooth substance, filling materials, from the suction current coming from the mouth of a patient.

Dental suction apparatuses include the so-called "wet systems" and "dry systems". In the wet systems, the current of air-secretion mixture is sucked from the suction canual, which is to be held in the mouth of the patient, by means of the suction machine through a pipe connection network. The techniques of production and of servicing and the operating costs of the piping system and the pumps are expensive. However, the main disadvantage is that in the piping system, the pump and like parts form a culture medium for the multiplication of bacteria. They are therefore very suspect from the point of view of hygiene.

In the dry system, a separation receptacle is provided in the neighbourhood of the patient's chair, into which receptacle the air-secretion mixture, which contains inter alia water, blood, saliva, tooth substance, filling material, is sucked. The air is therein separated from the liquid and solid components, which are precipitated, collected, and pass to the outflow, while the dry air is sucked through a clean air conduit system to the suction machine and blown off into the open. In the dry connections there is practically no danger of growth of bacteria.

In the conventional dry systems, these is provided a relatively large separation receptacle, in which the precipitation is mainly carried out by considerable enlargement of the cross-sections and consequent slowing-down of the air-secretion current. The precipitated liquid and solid components are collected in a relatively large receptacle and, on interruption of the suction, are automatically released in dependence on the negative pressure obtaining at certain points, or the absence of this negative pressure. In individual practical trails in certain countries, the separation has also already been carried out by centrifugal force. For various reasons, all these separation receptacles are unsatisfactory. The external dimensions of the separator are extremely large, and it can therefore often not be installed in the desired position in the work unit of the dentist, so that there must be provided relatively long connection leads to the separator receptacle, in which leads bacterial colonies can become established. The liquid-solid mixture collected in the receptacle comes to rest in at least a few places, so that the individual components separate and clumps or at least films are built up, which are culture media for bacteria and are very difficult to remove from the receptacle when the secretion is blown out, even though attempts have already been made by suitable choice of the shape of the apparatus to avoid material remaining suspended therein. The receptacle must therefore be opened at relatively short intervals and cleaned mechanically and by introduction of chemical cleaning and disinfecting media. For this purpose, it is opened by the assistant or the dentist, removed from the suction connections, and carried to the wash basin and there cleaned by hand and/or with brushes. Thus the bacteria which are present therein reach the space where the patient is treated and indeed the place where the treatment personnel as a rule clean their hands. A further drawback is that the dentist must break off work until the receptacle is emptied, when the maximum capacity is reached. Furthermore, very frothy media cannot be sucked off.

The invention aims to avoid or at least alleviate the above drawbacks and other drawbacks of the known separator receptacles, and achieves the advantages set out below.

The basic object of the invention is to produce a separation and precipitation device of the kind set out above, in which the solid and liquid components are separated from the suction current during the operation and are precipitated, and which is advantageously constructed from the point of view of servicing and above all hygiene, and which achieves a high degree of precipitation.

According to the invention, there is provided a separator for incorporation in dental suction apparatus, for separation of liquid and solid materials, such as water, blood, saliva, tooth substance, filling materials, from the suction current coming from the mouth of a patient, comprising a housing, which is provided with a separation chamber, an inlet for the suction current, an outlet for cleaned suction air, an outlet for separated liquid and solid materials, conduit devices for the suction current and air, and valves for the opening and closing of the outlets, and in which the separator components, which are contacted by the suction air and said materials form a unit which, with the exception of the inlet and outlets and control openings, if provided, is closed in operation and during cleaning and disinfecting, and is only disassemblable for repair; control and guide means are provided to maintain a constant movement of the separated materials in all places which are contacted thereby, and the liquid and solid outlet and internal flow cross-sections have sizes and shapes which do not hinder the flow of the liquid and solid materials.

The invention therefore has two substantially new features. One of these is that the receptacle or the whole device is always completely closed and therefore no bacteria can exit therefrom, and it is not necessary to carry out a cleaning operation which requires contact and would contaminate and render the hands of the assistant or the dentist dirty. The other is that a constant movement of the liquid and solid materials is maintained in the separation chamber, thus avoiding deposition of solid and liquid materials on the walls, or on the guide devices, valves or the like, since these are so constructed in respèct of their shape, their movability and in some cases their surface material that nothing deleterious can adhere thereto. Thus the principle of slowing-down of the flow of the solid and liquid constituents which are present in the suction media mixture is abandoned, and instead a system is adopted with a relatively fast movement of the solid and liquid constituents, preferably even with high dynamic force. Owing to the constant movement and to the design of the control and guide means, self-cleaning of the separator receptacle is made possible, so that opening is avoided and a practically permanently closed system can be achieved. The system only requires to be opened for repairs. To this end it is preferably provided with such closure means as can only be opened with tools, so that accidental unhygienic opening can be avoided.

The design of the various parts of the separator which are contacted by the suction mixture can be carried out in very many ways. Preferably an annular chamber is connected to the inlet opening, which chamber makes a smooth-surface transition into the separation chamber wall. In the annular chamber it is ensured that all surfaces are always in contact with the suction mixture current and are thereby cleaned. Nothing can therefore be deposited at the smooth-surfaced transition to the separation chamber wall. There are several possibilities for connecting the inlet opening to the annular channel.

It needs only to be ensured that the suction mixture current contacts the entire annular channel or annular channel part provided for the mixture current. Preferably the separation chamber has a round cross-section, since in this a constant movement can best be maintained. The annular channel should also have a circular annular shape, so that there results an equal degree of movement carrying the constituents forward at the parts which are contacted by the liquid and solid materials.

In a particularly advantageous form of the invention, the inlet opening leads tangentially into the annular chamber, so that there results a rotary movement of the suction current and thereby a separation through the operation of centrifugal force, which is particularly effective. Further advantageous curved surfaces can be provided in the annular chamber. These lead to an angularly directed flow, which can be supported by the formation of the tangential inlet cross-section. There then results a cyclone-type movement, which leads on the one hand to good separation and on the other hand to an effective carrying-away of the precipitated-out components from the on-flowing air.

The suction air can be led out of the separation chamber at various positions. It is particularly advantageous if it flows away within the inner wall of the annular chamber. There then results a direction reversal of about 180°. To this end, the suction air outlet is connected by at least one channel to an opening within the inner wall of the annular chamber. Preferably, the suction mixture current is directed downwards and the current of suction air within the inner wall of the annular chamber is directed upwards. The air current can more easily be sucked upwards and the solid and liquid constituents better collected and led off downwards. The suction mixture current carries out a helical movement. As the air current within the separation receptacle always contains a mist of liquid, and this also deposits on the suction conduit walls, there may be provided, according to a further advantageous novel feature of the invention, at least one suction nozzle arrangement on the inner wall of the annular chamber. As a result of the pressure difference and the difference in speeds, rising liquid is again sucked into the suction mixture current through these nozzles, so that the walls which border the air current are constantly dried. Advantageously, several suction nozzle openings are provided at different positions of height, so that the moisture can be sucked off at different heights. The various suction nozzle openings should also be arranged angularly offset from each other, so that they suck off the moisture which is drawn up with the suction current in accordance with the respective speed and moisture collection relationships in various regions. The suction nozzle openings should be so arranged, corresponding to the shape of the annular chamber and of the helices and the flow and moisture relationships, that they in each case open into the main suction mixture current at an advantageous position. In this respect, attention must be paid to the helical movement of the suction current. The helically formed guide surface in the annular channel needs only to extend through one complete circumference. The angles between the individual suction nozzles are preferably about 60° to 70°, and may be different from each other.

The annular chamber at the inlet should taper in the direction of flow, in particular downwards. The speed is then raised and the separation and precipitation improved.

To improve the sucking-off of residual moisture, there is preferably provided between the inner wall of the separation receptacle suction air channel and the inner wall of the annular chamber a further concentric, preferably slightly conical, residual moisture suction chamber, from which open suction openings of suction nozzle arrangements. Thereby, moisture collecting at the inner wall of the annular chamber and also running down on the inner wall of the separation receptacle suction channel, which hangs on the lower drip-edges, is led through the separate residual moisture suction chamber and the suction nozzles which lead out of this and is supplied to the suction mixture current, so that an even better degree of precipitation is achieved. The lower surfaces of the annular chamber borders are constructed as sharp and in some cases inclined drip-edges, thus improving the precipitation of liquid. In the highest region of the annular chamber there is preferably provided a suction arrangement leading to the separation receptacle suction channel, which arrangement is covered by a constriction of the separation receptacle suction channel, provided with at least one rejection edge and covering a dead water chamber extending to the suction nozzle inlet opening. Thus, just before the clean air chamber, the residual water collecting at the highest point is directly sucked off with a matching pressure.

Beneath the under-edge of the separation receptacle suction channel inner wall, there are advantageously provided roof-shaped or mushroom-shaped liquid rejection and precipitation surfaces.

It is further advantageous if a rotary insert is provided in the round receptacle. Thus precipitated liquid in the middle of the suction air current is thrown outwards by the rotating insert. This rotating insert preferably carries the mushroom-shaped fluid rejection and precipitation surfaces, so that the fluid can easily be thrown away from the outer edges thereof. The rotary insert is provided with vanes, which are driven by the suction mixture and/or air current which is rotating in a helical manner. Advantageously the vanes may be arranged on opposite sides and provided with straight surfaces. They then lead because of the rotating movement to a good drive, in spite of this. The vanes can be disposed in the separation receptacle channel, as the air here is already practically dry.

Below the separation chamber there are provided the secretion collection chamber part and/or the secretion collection chamber. These can be separated from the separation chamber by means of a partition provided with through openings. Advantageously this partition is shaped as a truncated cone, and is provided with corresponding through openings, through which the precipitated secretion can pass and also the air.

In the secretion collection chamber or in parts associated therewith, there may be provided sensor devices for the detection of the fluid level, which devices are in operative connection with the valves. No time-dependent control or control which depends on other measures of the dentist is then required, but the secretion collection chamber can be automatically emptied when a predetermined full state is reached. Overfilling can also be detected by these sensor devices. They can be of the mechanical, electronic, or pneumatic kind, and can be constructed in various ways. A float in the collection chamber forms a particularly simple sensor, favourable for maintenance of movement.

The float can be rotatably arranged around the central axis, so that it also contributes to self-cleaning. The shape of the float is advantageously formed by rotation of a trapezium. The secretion collection chamber may have an approximately conical outflow surface in its lower region, the smallest diameter of which forms the outlet opening. Also in the secretion collection chamber helical surfaces may be provided for the maintenance of the helical movement and/or the guiding of the precipitated liquid and solid material mixture, thus ensuring that the materials can be carried away without leaving any sediment.

The partition or spacing ribs may set the upper limit of the movement of the float and the helical guide surfaces may set the lower limit of the float movement. The float may be mounted on a rotary pipe which carries the vanes and in some cases the mushroom-shaped rejection surfaces. There thus results a single rotary body which is driven at various places but which is provided with several throwing-off surfaces. The rotary pipe may be arranged on a valve rod, which at its lower end carries the plate or plates of the outlet valve and at its upper end leads in a sealed manner out of the precipitation and clean air chamber and is there connected with the control devices. There thus results a simple, sound construction, in which the rotary pipe can be journalled on a part which would in any case be present, in a favourable manner with a large separation between bearings.

So that no constituents of the secretion current can be deposited on the valve parts, particular care should also be devoted to their design. Such deposition can be avoided by movement of the sealing elements. To this end, in a further advantageous form of the invention, the outlet valve is constructed with an elastic sealing disk lying on a fixed support disk, which sealing disk, during opening, first remains lying against its seating surface, and then buckles. A sudden tearing-away is avoided and a gentle opening achieved by provision in the elastic sealing disk of openings or cut-outs, whose inner borders lie on a diameter which is slightly larger than the seat of the outlet valve. These cut-outs or openings gradually release the cross-section on opening.

The separator device formed as above can with advantage be directly emptied at the outlet. However, care should then be taken that the emptying only takes place during the interruptions in the work of the dentist which are in any case necessary and also with large accumulations a substantially constant movement obtains in the closed receptacle. The self-cleaning and in some cases additionally the closed systems are much more easy to achieve if, according to a further advantageous feature of the invention, which is also important in its own right, the secretion collection chamber has a small volume in relation to the incoming flow, and, in connection with the secretion outlet opening, there is provided a drainage chamber with a further outlet valve.

So that here also there should be no accumulations and so that the rod stem can follow the other valve plate with the drainage chamber closed, there is provided between the drainage chamber wall and the further outlet valve plate a diaphragm which is clamped at the outer periphery thereof to the outlet opening, and which seals against the outlet valve plate and follows the movement of the valve rod.

Beneath the drainage outlet union there can be provided an intermediate collection receptacle which is open to the atmopshere and which is provided with a secretion removal connection. This is on the one hand favourable to holding the device, but is on the other hand most significant if, due to the spatial relationships which are imposed on the dentist, it is necessary to make an intermediate collection before leading away into a waste channel.

The separator device can be incorporated in variously constructed suction apparatuses, which in most cases in any case are provided with some form of suction air shut-off devices. It is not essential to provide a suction air shut-off device, but suction air shut-off is particularly advantageous, principally for three reasons. One of these is if the associated suction hose valves, which have various other functions, do not close in a completely sealed manner. Another reason is to be able to switch off individual separation receptacles, from a central installation, in particular however as an overfilling precaution against the case that the secretion outflow for any reason does not occur in the desired manner. The suction air shut-off device is for this purpose switched over if the liquid level reaches the overfilling device, and the suction air connection is then closed.

The operation of the various valves can take place mechanically, electromechanically, and/or pneumatically. The type of operation is determined by the insertion into the respective work place unit of the dentist. If the buoyancy forces of the float are sufficiently large, it may control its valves directly. Electrical operation of the individual valves is carried out conveniently with magnets. Any media currents can also be directly controlled with magnetic valves. Pneumatic control is however particularly advantageous, as there are in any case in the device negative pressure and pressure gradients, which can with advantage be used for the switching. Then the whole device can be supplied ready for operation as a complete unit without connection devices for external power.

For the ancillary provision of air to the operating control of the outlet valve(s), at the upper end of the rod stem there is provided a movable partition between a pneumatic control chamber and the clean air chamber. This movable partition can be sealed off with the aid of a diaphragm, because this, with good sealing, requires little force to overcome friction and if necessary hinders, by its flexing or rolling-up movement, deposition of undesired components.

Through the movable partition there may pass a sleeve device which transmits the motion of the float, and which is in operative connection with the control devices which control the opening of the secretion shut-off valve, this connection being pneumatic, electric, or optionally mechanical. The device operates in a particularly simple and secure manner if the sleeve device directly operates on a pneumatic valve. The valve element of this valve should be provided with two openings and a shut-off means which can selectively seal these off, and which can be held open in a middle position or may hold both openings open. For the emptying of the drainage chamber and a continuous separation operation with the outflow valve held pneumatically closed, a drainage chamber ventilation valve admitting atmospheric pressure into the drainage chamber may be provided. This can be operated mechanically, electromagnetically, or, in particular, penumatically. A pneumatic drainage chamber ventilation valve is controlled in a particularly simple and effective manner in dependence on the pressure in the control chamber above the movable partition. This ventilation valve is very simple and effectively operated if it is a diaphragm valve, the central opening of which is in communication with the atmosphere and of which the space surrounding its opening edge is in communication with the drainage chamber and whereof the valve chamber which lies on the surfaces of the diaphragm are remote from the opening and from the drainage chamber connection is connected with the control chamber above the movable partition.

For the activation of the pneumatic control chamber above the movable partition and of the suction air connection shut-off valve as an overfilling valve, advantageously a 3-position 3-way valve is used, on which a sleeve acts and which is provided with a closure body which is free and which moves perpendicularly up and down, which is provided with a downwardly projecting guide union, an annular seal surrounding this, and, on the upper surface, a flat seal, and which is provided with play and/or through-passage openings in the fixed partition between the control chamber and its own valve chamber and whereby the valve chamber can be connected with an atmosphere connection and the valve opening lying above can be connected with the overfill valve. This valve, which is simple and favourable in its construction and in its operation to the whole concept of the separator device, permits atmospheric air to be selectively allowed to enter the pneumatic control chamber. A further valve is then necessary for the supply of the negative pressure, which valve meters the negative pressure at an appropriate value. A sufficient difference in the areas can be achieved by corresponding forming of the surfaces. A connection can then be produced with a simple element leading through the movable partition between the clean air chamber and the pneumatic control chamber. This is achieved in that in the sleeve which transmits the rising movement of the float and penetrates the diaphragm there is provided a channel which, in dependence on the relative positions, opens, shuts off and/or increases through-openings for the vacuum, which channel permits the negative pressure obtaining in the clean air chamber to enter the control chamber to keep the secretion outlet valve shut. Further complicated valve members and channels in the housing can thereby be avoided.

In order to keep the outlet valve and the drainage chamber outlet valve open in a simple way under pressure equalization of the entire system, and to permit the whole amount of liquid to drain off, there is provided a spring, on which is supported the valve plate of the secretion chamber outlet valve and of the drainage chamber outlet valve.

The suction air connection or overfill valve can also be constructed in different ways; e.g., as magnetic valves. A particularly simple and effective solution provides a diaphragm valve, which includes a diaphragm which lies substantially horizontally and engages an upper annular seat. This valve can be produced economically and can be very effectively controlled in a completely pneumatic manner. Beneath the diaphragm there may be provided an annular chamber which surrounds the seat and is in communication with the clean air chamber of the precipitation receptacle, for the supply of suction air. Above the diaphragm is provided a control chamber, which is provided with valves for the supply of atmospheric pressure, suction pressure and controlled suction pressure. The controlled suction pressure can be created in a particularly simple manner by a suction jet nozzle arrangement open to the suction union. In the case of completely pneumatic control, in some circumstances at this point a signal reversal is useful, in which a large delay chamber is arranged between the channels coming from the suction jet nozzle arrangement and the 3-position 3-way valve and the control chamber lying above the atmospheric valve. Further peculiarities, forms, advantages and features of the construction according to the invention will appear from the following description with reference to the accompanying drawings.

Various embodiments of the invention will now be described with reference to the accompanying drawings, in which:

FIG. 1 is a vertical section through a separator according to a first embodiment of the invention, in which the section plane runs along the line 1—1 in FIG. 7; there is thus shown a vertical median section, in which the tangentially arranged inlet unions, which lie in front of the section plane, are however shown in the section plane; the device is shown in the initial or final position, in which atmospheric pressure obtains and no suction current is present, and also no liquid and solid constituents are present in the device.

FIG. 8 is a horizontal section along the line 8—8 in FIGS. 1-4.

FIG. 9 is a horizontal section along the line 9—9 in FIGS. 1-4.

FIG. 10 is a horizontal section along the line 10—10 in FIGS. 1-4.

FIG. 11 is a horizontal section along the line 11—11 in FIGS. 1, 2 and 4.

Figure 1:
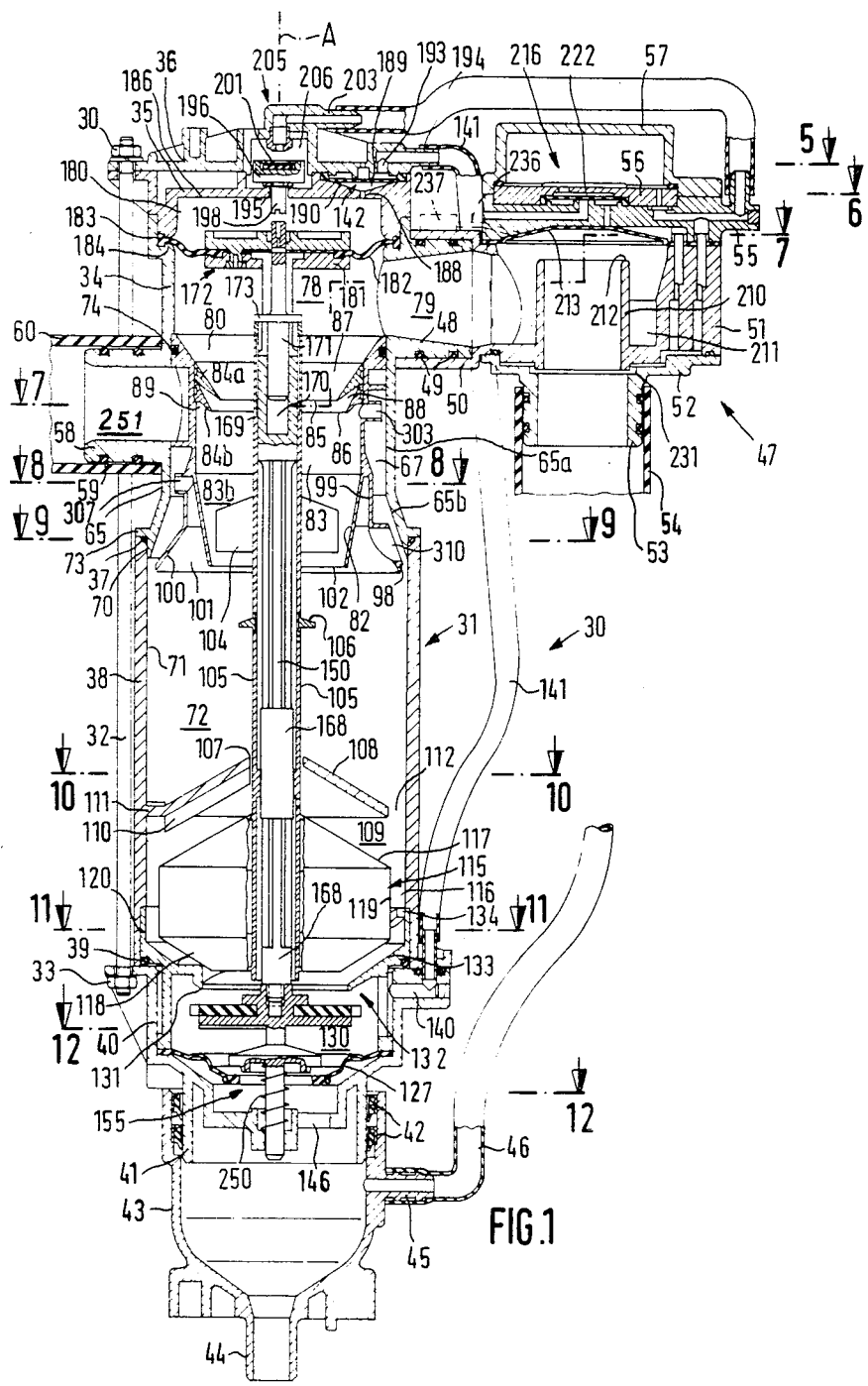
Figure 2:
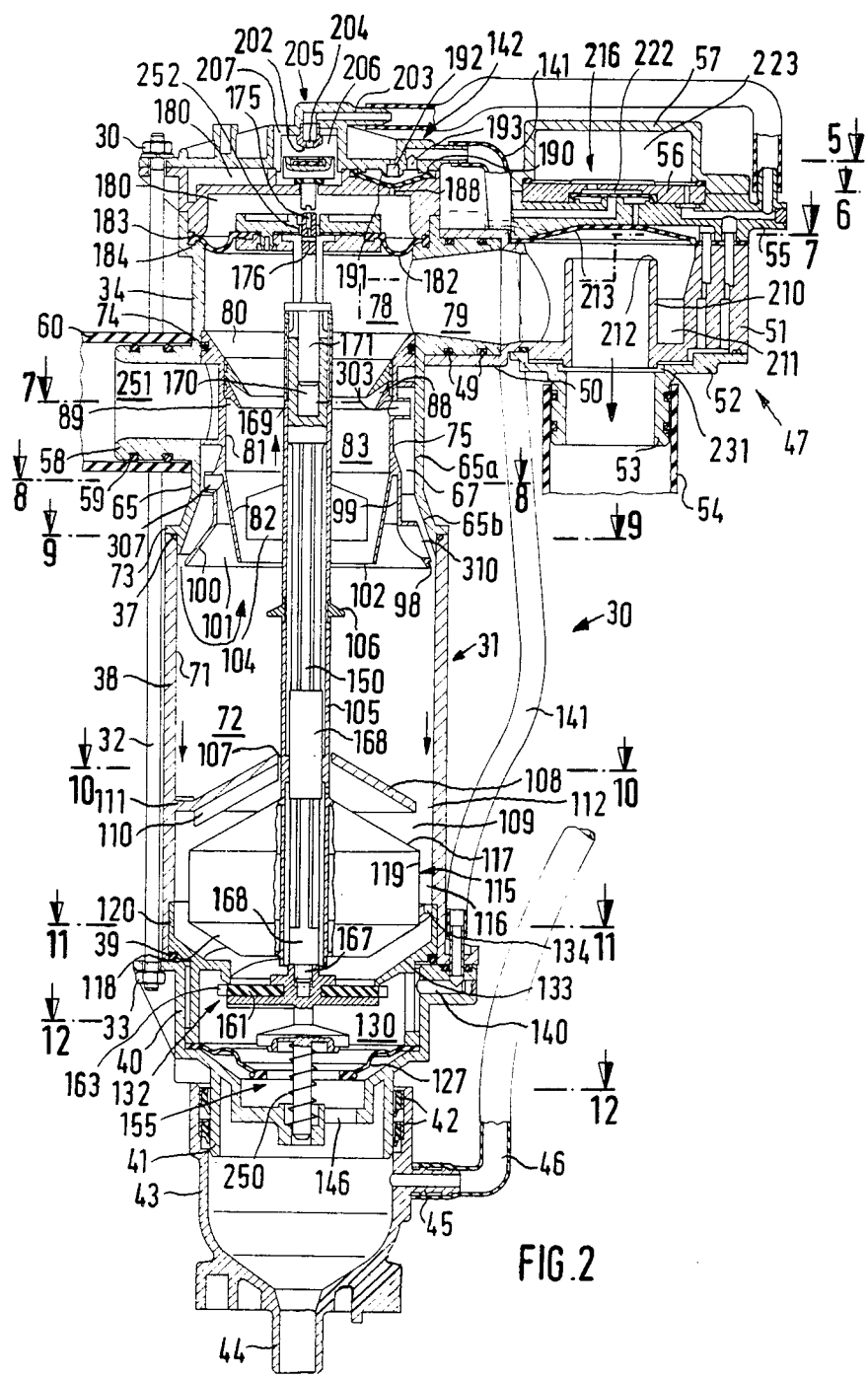
FIG. 2 is a vertical section corresponding to FIG. 1, in the operating position 1, in which the outlet valve is closed and the drainage chamber is empty.

FIGS. 1-16 show a separator 30 for separating solid and liquid constituents in dental suction apparatuses. For simplicity, "separating" is used for the three steps of separating the liqiid and solid components from the suction air stream, collection of such components and removal thereof, which steps happen partly together but partly independently. The separator 30 has a housing 31 consisting of several parts held together by tie rods 32, which at their upper and lower ends are provided with nuts 33, whereby the whole housing is always closed and is not normally opened by the dentist of his assistant. The parts can however be dismantled for repairs and general cleaning. An intake and air extraction part 34, which has a substantially round cross-section, is provided with a valve head 35, which is closed off by a cover 36. The part 34 is seated and sealed with a seal 37 on a cylindrical precipitating and secretion collection chamber part 38, to the bottom of which is connected a drainage part 40, sealed with a seal 39. On a cylindrical union 41 of the part 40 there is mounted, sealed with seals 42, an intermediate collector 43, which in its upper part is cylindrical and in its lower part approximately dome-shaped. This collector 43 is provided with a drain connection outlet union 44, on which can be fitted a hose (not shown), which may be connected to a drainage channel or to other dirt collection devices. It has an air extraction union 45 just below the seals 42, on which union is fitted an air venting hose 46, which leads to a level high enough to prevent any secretion from issuing therefrom.

The intake and air extraction part 34 has a union 48 for the cleaned air, on which is fitted the connection union 50 of a suction air shut-off valve housing 51, with sealing rings 49. At the underside of housing 51 is a suction air outlet part 52, close to but forming a gap with the housing 51, which suction air outlet part is provided with a suction air outlet union 53, on which is fitted the main suction hose 54 or a rigid pipe which leads to the suction machine. On the valve housing 51 there is a suction air ancillary valve head 55, in which is a valve intermediate disk 56, which is covered by a delay chamber cap 57. Between the individual parts are arranged seals, not all of which are shown, owing to the large number of parts. On an inlet union 58 of part 34 is fitted a suction hose 60 which leads to a suction base connection unit and further to the mouth of the patient. This hose is sealed with seals 59. A rigid pipe can be used instead of hose.

Figure 7:
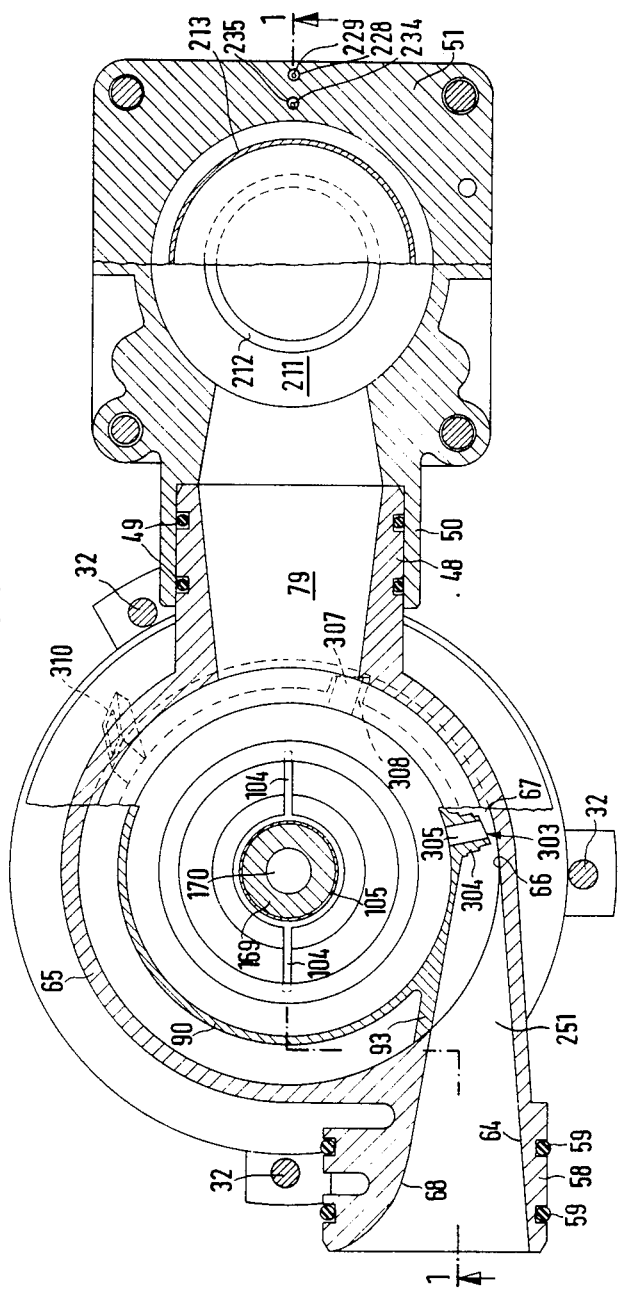
FIG. 7 is a horizontal section along the line 7—7 in FIGS. 1 and 2, which extends in the left-hand part through the inlet union and rises somewhat to the right of the central axis of the main receptacle to a higher plane which extends through the clean air channel, and in the middle of the shut-off valve suction union rises into a still higher plane in the shut-off valve.
Figure 12:
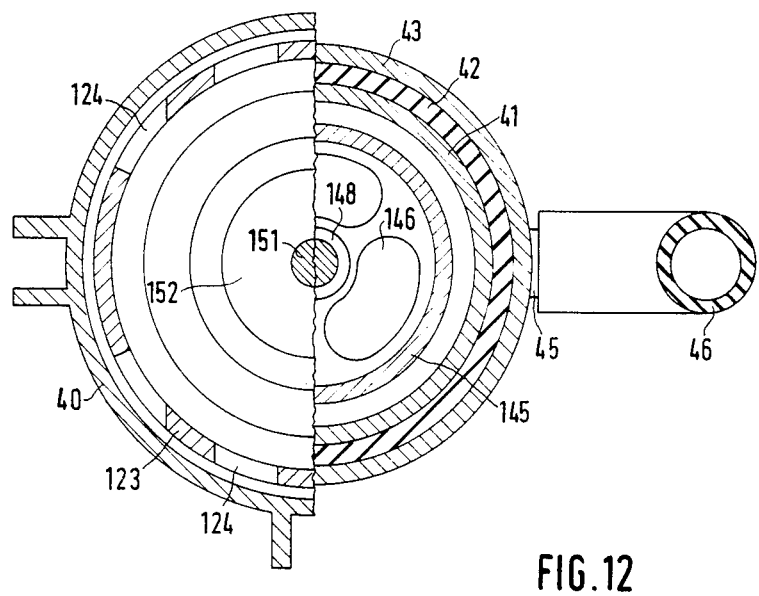
FIG. 12 is a horizontal section along the line 12—12 in FIGS. 1 and 2.

The part 34 has a substantially cylindrical outer wall 65, on which is radially formed the clean air union 48, the bore 79 whereof, as can be seen from FIGS. 1-4 and 7, widens slightly in the outwards direction. This union is in the uppermost region of the part 34. Somewhat beneath the middle of the part 34 in the inlet union 58, approximately on the opposite side to union 48. Its upper edge lies approximately at the same height as the lower edge of the union 48. It is outwardly round, but opens tangentially into the outer wall 65, as is shown in FIG. 7. Thus the wall 64 of the union 58 merges tangentially into the inner surface 66 of an annular channel 67 inside the part 34, while the wall 68 of the union is strongly narrowed and flattened (truncated) to form a nozzle 251, which leads gradually to the annular channel 67. The shape can be seen in FIGS. 1-4 and 7.

To the middle cylindrical part 64a of the outer wall 65 of the part 34, there is connected a wall part 65b, which broadens in the downwards direction and is slightly conical, and which terminates in a transition part 70 of triangular cross section, which makes a smooth transition, with smooth transitional surfaces, to the cylindrical inner wall 71 of a precipitation chamber 72 in the part 38. The part 34 is supported, with the addition of the seal 37, by a collar 73, on the part 38. A cyclone insert 75 is inserted into part 38 from below and sealed with a seal 74.

The cyclone insert 75 is shown in FIGS. 1-4, 7, 8 and 13. It has an upper collar 76, which is outwardly cylindrical and internally, as can be seen from FIGS. 1-4, conical, so that it is connected to the annular wall 77 of the clean air chamber 78 with smooth surfaces. The clean air extraction bore 79 is so arranged that its lower edge lies at the height of the upper edge of the conical part 80, to provide a smooth transition. In the interior, the cyclone insert 75 has a cylindrical inner wall 81, which extends over approximately half of its length, to which there is connected a separation receptacle suction channel wall 82, which is tapered in the downwards direction and is slightly conical, and which broadens in the direction of the current. In the uppermost part of the separation receptacle suction channel 83 there are two annular inserts 84a and 84b, which are provided with rejection- and drip-off surfaces 85 and 86 at their lower ends. The upper conical surface 87 of the annular insert 84a has approximately the same slope as the conical surface 80. The conical upper surface 88 of the lower annular insert 84b is somewhat more steeply inclined, so between the two annular inserts there is formed an intermediate chamber which has a sharply pointed triangular cross section. A dead-water space 89 is formed beneath the lower annular insert 84b. The outersurface of the cyclone insert is cylindrical over a height corresponding to the height of the inlet union 58 and carries, on this cylindrical surface 90, a helix 91, which extends through one complete circuit. The undersurface 92 of the helix is the upper boundary of the annular channel 67, this being sealed off at the inlet union by a transverse wall 93, so that the incoming medium is compelled to enter the annular chamber 67 bordered by the helix 91, and is thereby subjected to a helical movement. Beneath the lower end 94 of the helix the outer wall of the cyclone insert broadens in the downwards direction which a conical surface 95. To this is connected a cylindrical outer wall part 96, which as seen in FIGS. 1–4, is partly within the cylindrical wall part 65a and partly within the conical wall part 65b of the outer wall 65 of the part 34. To the cylindrical part 96 there is connected a conical surface 97, which widens in the downwards direction, and which terminates in a drip-off edge 98. The wall of the cyclone insert in this region is formed with uniform wall thickness, as can be seen from FIGS. 1–4, so that there are also formed in the interior a cylindrical surface 99 and a conical surface 100, which, together with the wall 82, which is likewise formed with the same wall thickness, define a residual moisture suction chamber 101, the entry opening 102 of the separation receptacle suction channel 83 lying somewhat above the edge 98.

Figure 13:
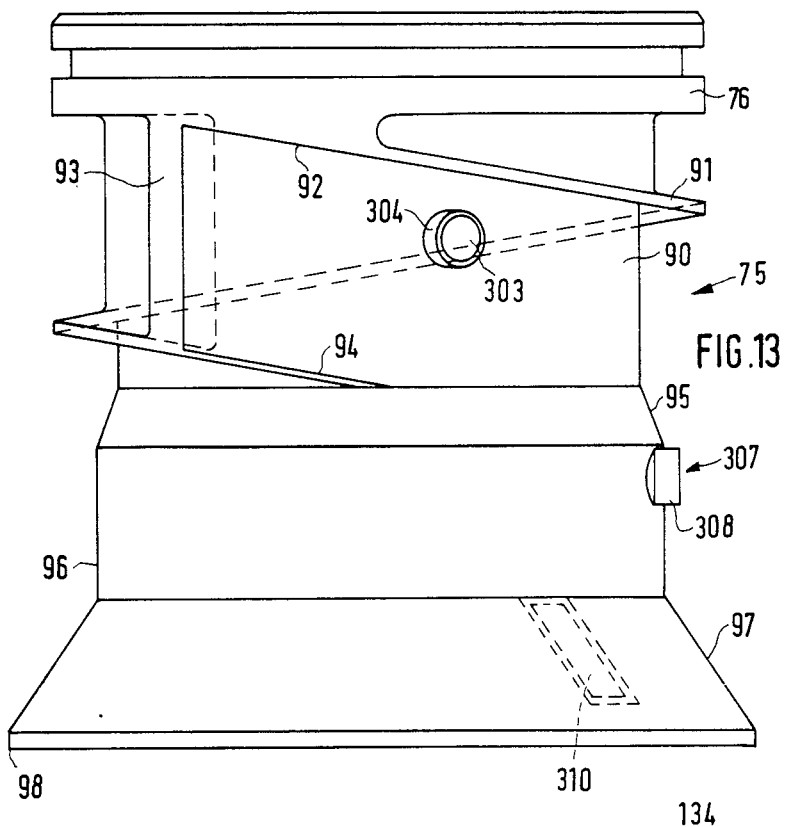
FIG. 13 is a magnified side view of the cyclone insert, removed, which defines the annular chamber, with the direction of view corresponding to FIGS. 1-4.

Three suction nozzles lead through the wall of the cyclone insert 75. As can be seen in FIG. 13, the first suction nozzle 303 stands, due to a collar 304, somewhat proud into the annular chamber 67. Its opening 304 opens out of the dead-water chamber 89. The mixed current of suction media in channel 67 pulls residual moisture out of the dead-water chamber 89 through the first suction nozzle 303 into the mixed current. As can be seen from FIG. 7, the second suction nozzle 307 is placed at an angle of approximately 60° from the suction nozzle 303 and is formed with a collar 308 in the cylindrical outer wall part 96; it extends from the uppermost part of the residual moisture suction chamber 101 and extracts moisture from the uppermost region thereof into the mixed current of suction media. In the lower region of the residual moisture suction chamber 101 the third suction nozzle 310 leads through the wall of the conical surface 97; this suction nozzle is offset with respect to the second suction nozzle 307 by an angle of approximately 70°, and is provided with an elongated rhombic cross-section with a corresponding neck. This nozzle sucks the major part of the moisture which is here taken up, into the mixed current of suction media, to throw it against the outer wall 71.

A rotating pipe 105 is rotatable about the vertical central axis A in the interior of the separator 30. This pipe carries, in the conical part 38b of the separation receptacle suction channel 83, two vanes 104 on opposite sides of the rotating pipe, which vanes have plane faces with a small separation from each other. As can be seen from FIGS. 1–4, these vanes have a trapezium shape. Close under the opening 102, a mushroom-shaped rejection surface 106 is formed on the rotating pipe. The rotating pipe penetrates an opening 107 in a partition 108, which is the upper boundary of the secretion collection chamber 109. The partition 108 is conical and has on its under-surface spacing ribs 110 and, between supporting ribs 111, large openings 112 which do not hinder the secretion flow.

Figure 14:
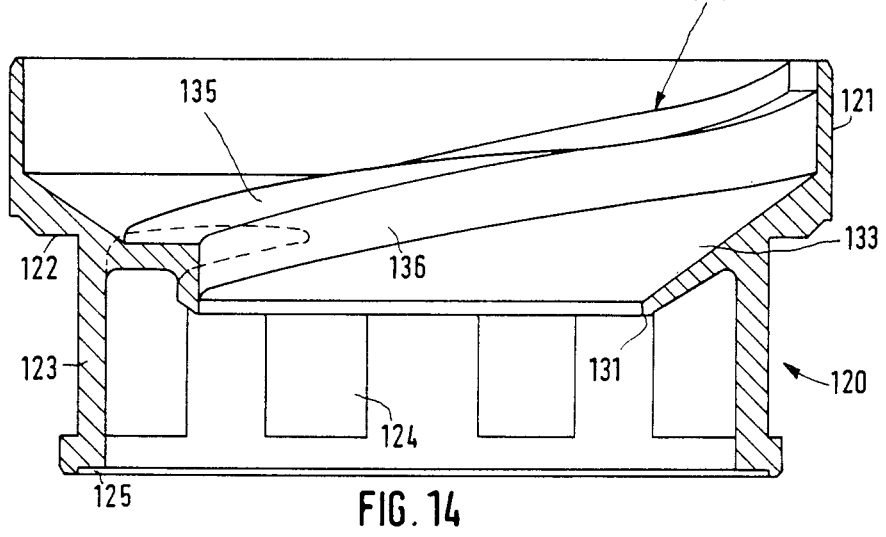
FIG. 14 is a magnified vertical section corresponding to FIGS. 1-4 through the removed secretion collection chamber and drainage chamber insert.
Figure 15:
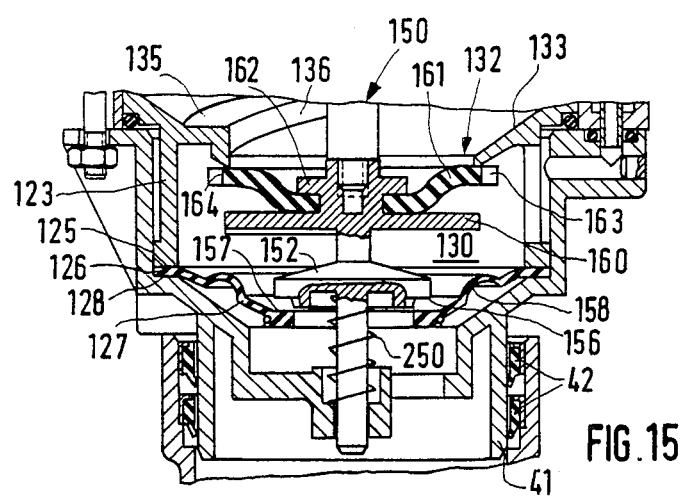
FIG. 15 is a magnified vertical part section in the same section plane as FIGS. 1-4 through the drainage chamber with the two outlet valves in an intermediate position, in which the sealing disc of the secretion collection chamber outlet valve is deformed, but has not opened.

On the lower end of the rotating pipe 105 is a closed hollow float 115, which leaves only a small annular chamber 116 in the secretion collection chamber 109. As can be seen from FIGS. 1–4, its shape is that generated by rotation of a pentagon, with upper and lower conical surfaces 117 and 118 inclined with respect to each other and a middle cylindrical part 119. The partition 108 extends parallel to the conical surface 117. In the lower part of the chamber 109 there is a drainage insert 120. Its details can best be seen in FIG. 14. It has a cylindrical upper outer surface 121, by means of which it fits the part 38, and a support shoulder 122 which rests on the part 40. A step is thus formed, which adjoins a cylindrical wall 123, which is provided with openings 124 and at its lower end has a clamping surface 125, with which it holds the outer edge 126 of a diaphragm 127 on an outlet valve 155 pressed on a clamping surface 128 in the part 40 (FIG. 15). The wall 123 is within the drainage chamber 130 of part 40. Above this chamber 130 there is formed in the insert 120 a seat 131 for an outlet valve 132. A sharply tapering, generally conical run-off face 143 extends from the cylindrical part 121 to the seat 131; on this face, as can be seen from FIGS. 11 and 14, are two helices 134, of which each extends around about a quarter of the circumference and which are provided with helical upper surfaces 135 and vertical helical side surfaces 136, and, as shown in FIGS. 10 and 14, project from the conical run-off surface 133. Between the insert wall 123 and the vertical wall 138 of the part 40 there is formed an annular chamber 139, which is connected with the drainage chamber 130 through the openings 124 and which communicates with a ventilation connection 140, to which is connected a ventilation hose 141, which leads to a ventilation valve 142. To the cylindrical wall 138 there is connected a downwardly tapered wall 144, which adjoins a cylindrical projection 145, in the bottom of which there are openings 146 between holding ribs 147. The ribs 147 carry a rod bearing 148, in which the lower end 149 of a valve rod 150 is guided in a vertically movable manner. Between the bearing 148 and a valve plate 152, which is formed on the screw-threaded lower part 151 of the rod 150, there is arranged a weak compression spring 250, which is so chosen that when the entire separator is at atmospheric pressure, it holds the valve rod 150 with all the parts bearing thereon at such a height that the secretion collection chamber outlet valve 132 and the drainage chamber outlet valve 155 are open. The drainage chamber valve plate 152 has a closure surface 156, against which a closure lip 157 of the diaphragm 127 can lie in a sealing manner, if appropriate pressure relationships exist, so that the diaphragm can then also follow the movement of the valve plate 152. So that it can easily follow this movement, the bead shown by way of example at 158 in FIG. 15 may be provided. The diaphragm consists of an elastic material, preferably of a synthetic plastics material, which is insensitive to the media to which it is exposed, and allows a good wiping clean of the diaphragm surface and is provided with a smooth surface which repels the secretion constituents.

Figure 16:
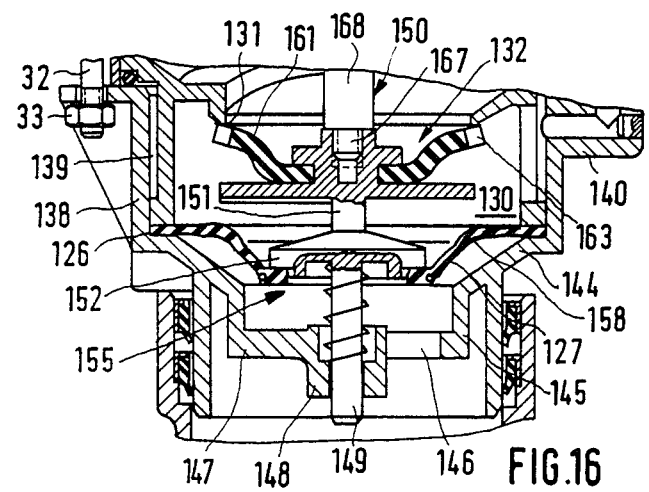
FIG. 16 is a representation corresponding to FIG. 15, at the instant in which the outlet valve has just opened.

The outlet valve 132 has a fixed valve plate 160 formed on the screw part 151, which valve plate has approximately the same size as the seat 131 and is round. On it lies an elastic sealing disk 161, which is fixed to the valve plate 160 with the aid of a holding ring 162. The holding ring 162 has however a substantially smaller diameter, as can be seen from FIGS. 15 and 16, so that the elastic sealing disk 161 can buckle upwards. The elastic sealing disk 161 has several cut-outs 163 in its edge, distributed over its circumference, the inner limit 164 of which cut-out lies on a diameter which is somewhat larger than the diameter of the seat 131. The result of this is that when the pressure in the chamber 130 is larger than that in the precipitation chamber 72 and rod 150 moves downwards and, as shown in FIGS. 15 and 16, the elastic sealing disk is thereby buckled and the passage cross-section is gradually opened, and the sealing elements also thereby wiped, so that no disadvantageous setting of the components of the secretion can occur. Instead of cut-outs, through-holes may also be stamped out or otherwise formed in the sealing disk. The screw part 151 is screwed onto the rod stem with the aid of the thread 167, to facilitate assembly. The valve rod 150 has a cruciform cross-section and individual rotary bearings 168 separated from each other, to make possible easy motion in the rotating pipe 105 and an easy run of the rotating pipe on the rod. The valve rod 150 carries a slidable stem 171 in a bore 170 in its upper bearing 169, which stem penetrates a movable partition 172. The stem 171 has support ribs 173, which are supported on the rotating pipe 105 and follow the movement thereof in raising and lowering of the float 115. The stem 171 is freely guided in a bore 252 in the movable partition and has an axial bore 175, which joins a transverse control bore 176, which, depending on the valve setting, connects the pneumatic control chamber 180 and the clean air chamber 78 with one another to a greater or smaller extent. The movable partition 172 is tightly connected with the rod 150, so that this, and thereby the valve plates of the valves 132 and 155, can follow the movement of the movable partition 172. The movable partition includes a rigid middle part 181, which is rigidly connected to the rod 150, and in which a diaphragm 182 is clamped. This diaphragm consists of an elastic material, which allows the movements shown, is insensitive to the media present and in some cases impedes setting of undesired components. It is furthermore so formed that it can be cleaned and in a certain sense works as a roll diaphragm, as shown in FIGS. 1–4. The outer edge 183 is tightly clamped between a sealing wall 184 of the part 34, and the valve head 35. The valve head has a cylindrical flange which encircles the pneumatic control chamber 180, and an upper closure wall 186. In this are formed two passages. The control bore 188 connects the control chamber 189 of the drainage chamber ventilation valve 142 with the pneumatic control chamber 180. The chamber 189 is formed by a conical wall and a valve diaphragm 190 with a thickened edge tightly clamped with the aid of the cover 36. A downwardly directed sealing seat 191 for the valve diaphragm 190 is formed on the cover 36, with a central opening 192 open to the atmosphere. Beside the seat 191, a connection channel 193 leads to a union 194, on which is fitted the ventilation hose 141, so that when the diaphragm 190 is raised the chamber 130 is connected to the atmosphere through the valve 142.

In the other cover opening 195 there is a valve element 196 of a 3-position 3-way valve 205, normally closed by its own weight. The cover opening has a sealing edge 197 forming a valve seat. The valve element has a valve stem 198 guided with play in the opening 195, which valve stem carries, under the valve piston 199, a ring seal 200. On the upper side of the piston there is provided a flat seal 201 facing a seat 202 with a central bore 204 connected to a connection union 203 of valve 205. An atmosphere vent 207 also opens into the valve chamber 206 of the valve. The dimensions of the rod 150 and of the valve stem 198 and the relative positions of the seals and seats are so chosen that in the position of maximum height of the float 115, the flat seal 201 closes the seat 202 and thus no air from the atmosphere can enter the union 203 and the overload valve 47. When the float 115 has fallen, and in all intermediate positions until the normally provided maximum secretion filling before emptying, the annular seal 200 rests on the seat 197 and prevents the entry of atmospheric pressure into the pneumatic control chamber 180. When the float reaches the "full" position, the annular seal 200 is lifted and provides a connection from the pneumatic control chamber 180 to the atmosphere.

Figure 3:
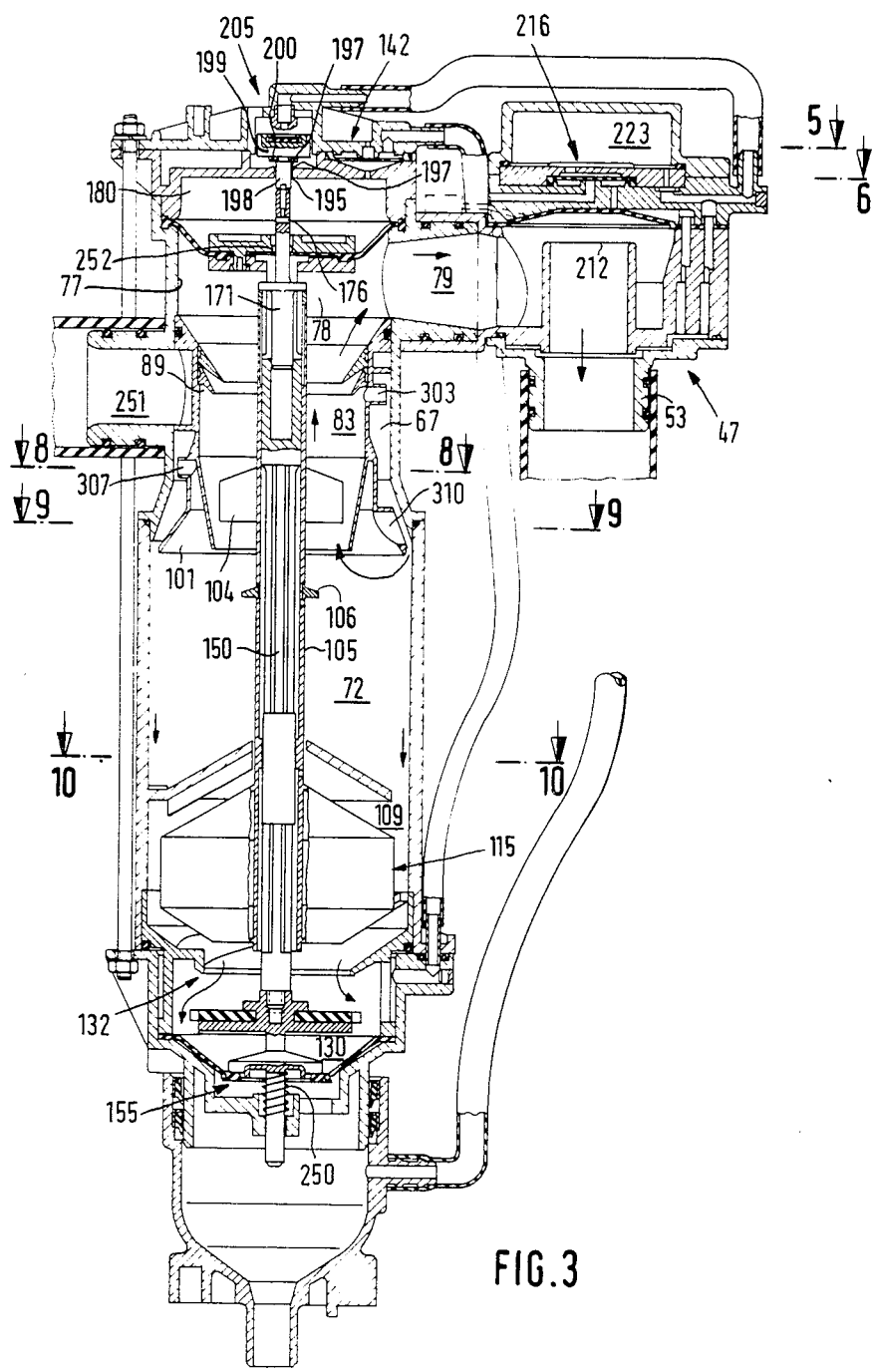
FIG. 3 is a vertical section corresponding to FIGS. 1 and 2, in the operating position 2, in which the drainage chamber outlet valve is closed and the outlet valve of the secretion collection chamber is open, so that the secretion has collected in the drainage chamber.
Figure 4:
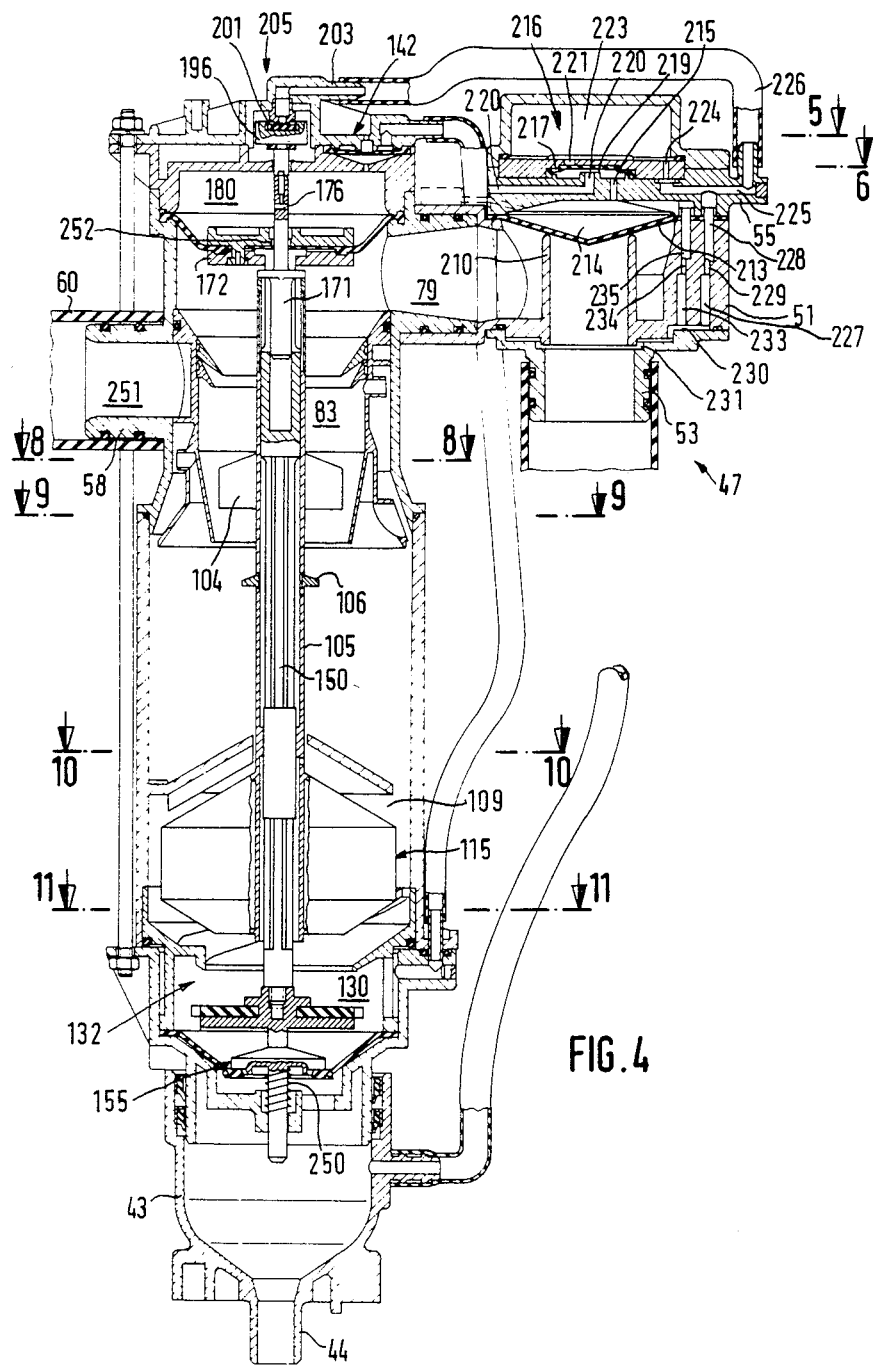
FIG. 4 is a vertical section corresponding to FIGS. 1-3, in the overfilled position, in which the suction connection is just shut off, but the drainage chamber outlet valve is still closed.
Figure 5:
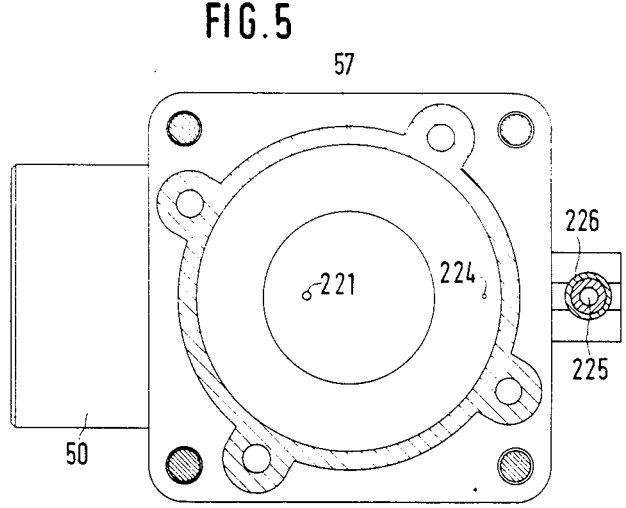
FIG. 5 is a horizontal section along the line 5—5 in FIGS. 1-4.
Figure 6:
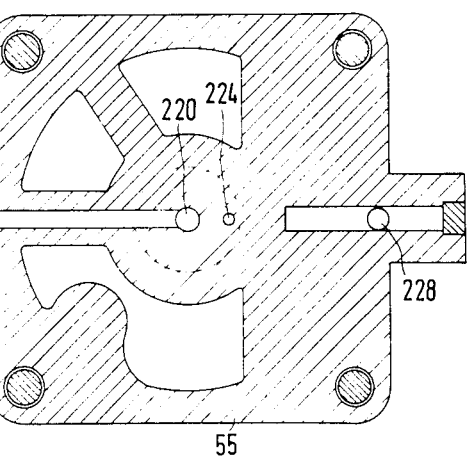
FIG. 6 is a horizontal section along the line 6—6 in FIGS. 1-4.

The suction air shut-off valve 47 has in its housing 51 a shut-off valve suction union 210, which is located in an annular valve chamber 211 and has at its upper end an annular seat 212, on which a sealing and switching diaphragm 213 can lie in a sealing manner. This diaphragm is clamped between the valve housing 51 and the suction air ancillary valve head 55, and also provides the sealing for various passages between these two parts, the diaphragm having holes corresponding to these passages. The diaphragm bounds a control chamber 214, which is formed with several connection channels (FIG. 4). The connection channel 215 leads to a control chamber ventilation valve 216, which is provided with a diaphragm 217 clamped between the suction air ancillary valve head 55 and the ancillary valve disk 56 and can rest on a seat 219 which surrounds an atomsphere conduit 220. Above the diaphragm 217 there is formed a small control chamber 222 which is connected through a bore 221 with a delay chamber 223. The delay chamber 223 is in connection through a bore 224 with a passage 225, which is connected on the one hand through the hose 226 with the union 203 of the valve 205 and thence can be actuated by atmospheric pressure. On the other hand it is connected with a suction jet nozzle channel 228. This channel has a throttling constriction 229 and terminates downwards in an annular gap 230 between the valve housing 51 and the suction air connection part 52, which is constructed in a stepped manner and is provided with an inner smaller annular gap 231, which is formed between the shut-off valve union 210 and the suction air connection union 53, so that the difference in diameter which can be seen from FIGS. 1–4 is produced. The main suction current which passes through the union 53 at this point creates at the small lateral gap 231 a high negative pressure by suction jet nozzle operation of the Borda-nozzle type, which pressure can be used for control purposes in his ancillary valve. The throttle 229 prevents the undesired influx of excess air from the atmosphere. A further passage 233 is connected to the annular gap 230 and has a throttling constriction 234. Its upper part 235 opens into the control chamber 214. If desired, a further atmosphere passage 236, shown in chain lines, may be provided, leading to a magnetic valve, which can be provided if required, if it is wished to turn the whole separator on and off remotely by electrical means by letting in atmospheric pressure or shutting this pressure off; for example, if several separators 30 are used with one suction machine, individual separators being used at different times. The housing parts, inserts and valve elements consist of synthetic materials which are insensitive to the media present and which form smooth surfaces. Preferably they are produced by injection moulding.

Operation

The described separator 30 operates as follows:

When the suction apparatus is not in operation, atmospheric pressure is present in all parts of the equipment and consequently also in the separator 30. The compression spring 250 then holds the rod stem 150 with its screw part 151 and consequently the valve plates 152 and 160 in a middle position, so that the outlet valve 132 and the sluice outlet valve 155 are open. Whole secretion; i.e., liquid and solid components, can leave the secretion chamber 109 through the chamber 130 and the openings 146 and flow to waste through the outlet union 44. The float 115 has sunk to its lowest position. The valve diaphragm 190 is under its own tension and lies against the seat 191 to close the atmosphere bore 192. The sleeve 171, like the float 115, is in its lower position. Consequently, the valve element 196 can sink under its own weight so that the annular seal 200 closes the valve bore 195 leading to the pneumatic control chamber 180. The diaphragm 217 in the control chamber ventilation valve 216 lies on the seat 219 freely and closes the atmosphere conduit 220. The diaphragm 213 is in a middle position, which depends on its own tension due to its conical shape, since on both sides thereof the same pressure exists, and the suction air shut-off valve 47 is in the "open" position. The separator 30 is in the terminal or initial position shown in FIG. 1.

Operating State 1

The suction machine is started to effect exhaustion. This occurs in various ways depending on the setup of the dentist's surgery; for example, by taking a suction mouthpiece holder from its bracket on a holder device, whereupon an electrical switch is operated, which starts the motor of the suction machine. There now exist a negative pressure at the suction air connection union 53 and an air current through the whole separator 30. By the airflow in the union 53, the pressure in the annular slot 231 is reduced with respect to the pressure directly under the diaphragm 213. The annular slot 231 is connected to the control chamber 214 through the annular slot 230, the passage 233, the throttle 234 and the passage 235. Owing to the interposition of the delay chamber 223, the control chamber ventilation valve 216 remains closed and the negative pressure at the annular slot 231 communicates with the control chamber 214, so that the diaphragm 213 is sucked upwards and the seat 212 becomes free and thereby makes possible the passage of suction air through the bore 79, the suction channel 83, the annular channel 67 and the inlet union 58.

As the valve element 196 is in its lowest position, more air can flow in from the atmosphere through the bores 207 and 204 and the hose 226 than can be drawn off through the throttle 229, so that the valve 216 remains closed and the valve 47 remains open.

The pressure in the clean air chamber 78 under the movable partition 172 falls. As the pneumatic control chamber 180 is in communication, through the bore 252 for the stem 171, with the clean air chamber 78, and the seat 197 is closed by the annular seal 200 of the valve element 196, the same lowering of pressure occurs in the pneumatic control chamber 180. On both sides of the movable partition 172 there is now the same negative pressure; however, the operative surface areas on the two sides of the movable partition 172 differ by the cross-section of the stem 171. The result of this is that the movable partition 172 is sucked upwards. The pressure simultaneously falls in the precipitation chamber 72, while in the drainage chamber 130 atmospheric pressure obtains. Thus the pressure difference acts on the valve plate 160, thus assisting the lifting movement of the rod 150, which is counterbalanced by the spring 250. The sealing disk 161 now reaches the seat 133 and closes the outlet valve 132. The chamber 130 is now separated from the secretion collection chamber 109.

Because of the negative pressure which is building up in the pneumatic control chamber 180, the valve diaphragm 190 of the ventilation valve 142 moves away from the seat 191, so that the atmosphere is connected to the ventilation hose 141 and thereby to the chamber 130. The pressure in the chamber 130 remains atmospheric, and the diaphragm 127 is spaced from the valve plate 152, so that the chamber 130 is connected with the waste outflow. The operating position shown in FIG. 2 has now been reached.

Separating in the Operating States 1 and 2

The air, which reaches the separator 30 from the mouth of the patient through a suction canula, in some cases a connection device, and the suction hose 60, is rich in saliva, blood, pus, dentine-powder, amalgam, etc. Large solid particles are removed by a preliminary filter. Much the largest quantity of dirt passes this preliminary filter and enters the separator through the inlet union 58. The mixed current is considerably accelerated by the nozzle 251 and tangentially enters the annular channel 67, where it is forced into a cyclone-type rotary movement by the arrangement of the nozzle and by the helix 91/92. The liquid and solid constituents are hurled against the outer wall 65 by the centrifugal forces acting on them. Even blood foam, which is contained in the air, can be separated by the centrifugal forces, being forced to collapse by the centrifugal forces. The air and secretion current is guided and accelerated corresponding to the form of the annular channel 67, as it pursues the rotary movement into which it is forced. In the precipitation chamber 72 between the partition 108 and the opening 102 the air, which is now nearly free of liquid and solid material, exits downwards from the annular channel 67, is turned through approximately 180° in the upwards direction, reaches the clean air chamber 78 through the channel 83, and from there proceeds through the valve 47 to the suction air outlet union 52 and from there to the suction machine.

Water and secretion droplets not only flow down on the outer walls 65 and 71, but also remain hanging on the outer surfaces 90, 95, 96 and 97 of the cyclone insert 75 and gradually make their way downwards. On the bending of the air stream through 180°, the smallest water droplets are torn away from the inner wall 71. These water droplets collect, rotating, on the edge 98. So long as they do not drip off, some parts thereof are dragged by the air stream around the drip-off edge of the inlet opening 102 and make their way upwards with the air in the channel 83 or else reach the residual moisture suction chamber 101. The suction nozzle 310, of which the end, which is cut off at an angle to the air stream and is rectangular, projects into the annular chamber 67 in the zone of the largest local air speed in this region, acts as an injector, drawing most of the collection of water films and secretion films formed of rising drops, from the chamber 101 into the suction mixture current for further separation by centrifugal force and flow to the inner chamber wall 71. The separated liquid and solid material passes through the openings 112 in the secretion collection chamber 109 in a rotary movement. Owing to their mass, solid particles can hardly reach the channel 83. Liquid drops, which are not caught by the lowest suction nozzle 310, make their way in the residual moisture chamber 101 again in the upwards direction, and are caught by the suction nozzle 307, which is shaped as a pipe, and are finally drawn out into the annular chamber 67. The suction mixture stream has its maximum speed directly downstream of the nozzle 215. Its speed gradually decreases due to expansion in the annular channel 67 and due to friction. Thus the suction nozzle 303 lies at the position of maximum flow speed, the suction nozzle 310 lies at a position of medium flow speed, and the suction nozzle 307 lies at the position of relatively least flow speed in the course of the suction mixture current. The suction nozzles 303, 307 and 310, with their necks, cross-sectional forms and cut-off end surfaces, are so dimensioned that they produce optimal relationships at their respective positions, and in particular in respect of the highest flow speed in the suction channel in each case, which is at a position remote from the walls.

The suction nozzles are shaped as can be seen in the drawings and are cut off at an angle, which improves their operation. The suction nozzle 303 has the task of sucking the small residual liquid droplets in the channel 83, or a secretion film climbing up the wall of this channel, from the dead water chamber 89 with high negative pressure into the suction mixture current in the annular chamber 67, to optimize the degree of separation of the separator 30.

The annular inserts 84a and 84b are provided to facilitate a favourable flow form and promote secure retention of liquids, so that the air which is drawn into the clean air chamber 78 is free of water and secretions. This separation, precipitation and sucking-off process of residual liquids is carried out independently of the valve settings, so long as there is a suction current through the separator, which, due to the different guiding means, always executes a rotating movement.

The secretion current which, in a helically downwards movement, has reached the secretion collection chamber 109, rotates the float 115, provided on the rotating pipe 105. This rotary movement is assisted by the vanes 104. Liquid collecting on the rotary pipe 105 is thrown outwards from the rejection surface 106 and is mixed with the downwardly flowing secretion current or jointly precipitated on the walls of the cyclone insert in the manner described above.

The water-secretion-solids-mixture flowing into the chamber 109 slowly causes the liquid level to rise. The float 115 is also thereby raised and, with the aid of the stem 171, raises the valve body 196, while the upper end of the stem 171 meets the valve rod 198. The annular seal 200 is thus lifted away from the sealing edge 197, so that atmospheric pressure can slowly enter the pneumatic control chamber 180. Under the difference of forces now acting on the movable partition 172, this moves in the direction "open"; i.e., down, and, through the rod 150, presses the valve plates 160 and 152 downwards. This process is carried out very slowly, and at first the sealing disk 161 remains pressed onto the seat 131, by the pressure difference between chambers 130 and 72. The sealing disk 161 is thus deformed in a bell-shaped manner (FIG. 15). The valve plate 152 is brought close to the diaphragm 127. The cut-outs 163 now permits a slowly increasing pressure equalization between chambers 130 and 109 (FIG. 16). The ventilation valve 142 closes under the effect of the atmospheric pressure which is building up in the pneumatic control chamber 180 and thereby in its valve chamber 189 through the control bore 188, and thereby disconnects the chamber 130 from the atmosphere. The diaphragm 127 is now sucked onto the valve plate 152 under the negative pressure operating in the chamber 130, so that its sealing lip 157 lies sealingly on the sealing surface 156 and thereby closes off the chamber 130 from the outflow. The sealing disk 161 now snaps off from the seat 131, and the mixture of water, secretion and solids flows out of the secretion collection chamber 109 into the drain chamber 130. The operating position 2 shown in FIG. 3 is thus reached. The float 115 falls, with the rod stem 150, back into its initial position. This also causes the stem 171 to descend, releases the valve 205 and thereby disconnects the pneumatic control chamber 180 from the atmosphere. Simultaneously the transverse control bore 176 is opened and this makes possible a rapid pressure equalization between the clean air chamber 78 and the pneumatic control chamber 180. The rod 150 is rapidly raised by the negative pressure which is building up in chamber 180, owing to the surface-area difference. The valve plate 160 presses the sealing disk 161 sealingly against the seat 131, so that the outlet valve 132 is rapidly closed. The diaphragm 127 follows this movement and only drops away after the closure of the outlet valve 132, when the ventilation valve 142 has opened and atmospheric pressure is allowed to enter the chamber 130. The solid and liquid components can now pass out of the chamber 130 through the openings 146 into the receptacle 43 and from there, through the outlet union 44 to a waste-water channel or another collection and cleaning location.

This sequence of discharging liquid and solid components from the precipitation chamber 72 through the secretion collection chamber 109 and the outlet valve 132, the chamber 130 and the valve 155 to the outlet, occurs continuously during the suction process according to the incident amounts, in small amounts. In this connection, the chamber 109 and the float are so dimensioned that only a relatively small amount of liquid and solid material is collected before being transferred into the chamber 130, whereby the precipitated components are always in motion and nothing is removed therefrom, and furthermore the rotating motion is transmitted through the large opening in the outlet valve 132 into the chamber 130, and here, as a result of the rapid through-drainage, also leads to a continuous motion, and the wiping of the sealing disk 161 and the diaphragm 127, as can be seen from FIGS. 15 and 16, contributes thereto, "sedentary" solids being finally detached and admixed with the fluid stream, so that these valves have a self-cleaning effect.

Advantageously, the separator 30 is so dimensioned that the maximum amount of water, secretion and solids that can be processed per unit time approximately corresponds to the maximum amount obtained in treatment of one patient. However, during the treatment, smaller amounts of separated materials are drained off many times, so that the retention time is very short. This is a considerable advantage compared with the conventional precipitators, because a constant movement of the separated constituents is thereby facilitated and consequently, together with other measures, a constant self-cleaning of the separator takes place, to such an extent that it only needs to be flushed through with a cleaning and disinfecting medium after the end of the day's treatment. For this purpose, the suction nozzle, which is normally held in the mouth of the patient, is held in a cleaning and disinfecting medium, which is automatically sucked through the separator and all the parts contacted in use by liquid and solid, and this medium is transported in the same way as described above through the drainage chamber, so that both this and the outflow are cleaned and disinfected. Owing to the high incident speeds of the mixture current and/or the insertion of a drainage chamber, the separator can be made particularly small. It has altogether only about the size of a human forearm and can therefore with advantage be installed in the neighbourhood of the suction canula, so that only very short connections, which are contacted by dirty suction mixture, are required. The separator does not need any mechanical cleaning by the assistant or opening of the device, so preventing the egress of bacteria into the working space of the dentist. A high degree of precipitation is achieved, comparable with that of the conventional large separator receptacles; in spite of this, however, the external dimensions are substantially smaller. The dentist can work continuously, as the waiting time until the separator receptacle is emptied is dispensed with. The separator according to the invention is however provided with an overflow protection device. This comes into operation if such a large quantity of liquid is sucked in that the through drainage cannot occur with sufficient rapidity, or if any of the valve parts fail. Particularly, it comes into operation if disinfection is carried out in a careless manner; i.e., if for disinfection purposes large amounts of liquid are sucked in for a long time. If the float rises again as far as the middle position of the valve element 196, the flat seal 201 finally reaches the seat 207 of the valve 205. Thus no more air can enter from the atmosphere through the hose 226 to reach the delay chamber 223. The suction nozzle arrangement will now, through the annular slot 231, establish a negative pressure in the delay chamber 223 through the passages 227, 228, 225 and the bores 224, 229, which raises the diaphragm 217 so that atmospheric air can enter through the atmosphere channel 220 and the bores 219 and 215 into the control chamber 214. The amount of inflowing atmospheric air is greater than the amount of air sucked through the throttle 234, so that a higher pressure acts on the upper side of the diaphragm 213 than on the underside thereof. The diaphragm 213 is thereby pressed onto is associated annular seat 212, and thereby shuts off the suction air outlet union 53. Atmospheric air can now enter through the inlet union 58. The compression spring 250 moves the rod 150 into the middle position, the valves 132 and 155 open, and the entire amount of liquid flows out of the precipitation chamber 72 and the secretion collection chamber 109 and away through the chamber 130. When the receptacle is empty, the float 115 descends, the valve 205 allows the valve body 196 to descend again and the bore 204 to open, so that atmospheric air again flows into the delay chamber 223. At the inlet of the chamber 223, a throttle is formed in the bore 224. The rise in pressure in chamber 223 requires a certain time, so that the closure of the atmosphere connection 220 by the diaphragm 217 and thereby the opening of the diaphragm 213 occur with a time delay. This time delay makes it possible for the liquid and solid materials also to flow out of the chamber 130. When the diaphragm 213, and thereby the suction air shut-off valve 47, open, the separator is then again in the operating state 1 shown in FIG. 2. A phase of the overflow state before the opening of the valve 155 is shown in FIG. 4, while FIG. 3 shows the operating state 2, in which the outlet valve 132 is open. If a negative pressure continues to exist at the suction air outlet union 53, the separator goes from the overflow state into the operating state shown in FIG. 2. If there is no negative pressure, the separator assumes the initial or final state shown in FIG. 1. If, with negative pressure present at the suction air outlet union 53, the separator is to be put out of operation and a magnetic valve 237 is provided, this valve may be opened electrically. Atmospheric air then enters the control chamber 214 through the atmosphere channel 236 and the diaphragm 213 closes its seat 212, so that atmospheric pressure can be reached in the whole separator 30, as there is no suction air stream. This additional device is used when several separators 30 are connected to a single suction machine and these separators are to be switched on and off as required, preferably by electrical switches coupled with the suction hose holders.

Figure 17:
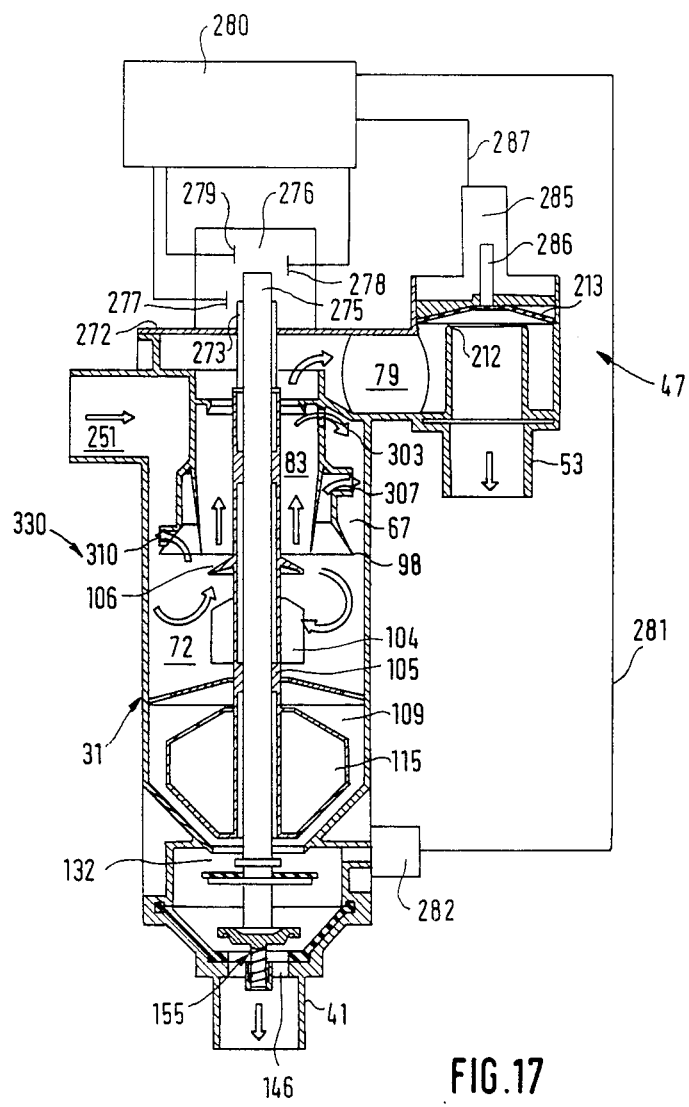
FIG. 17 is a highly schematic vertical section through a second embodiment of the invention with schematically shown alternative control devices.
Figure 18:
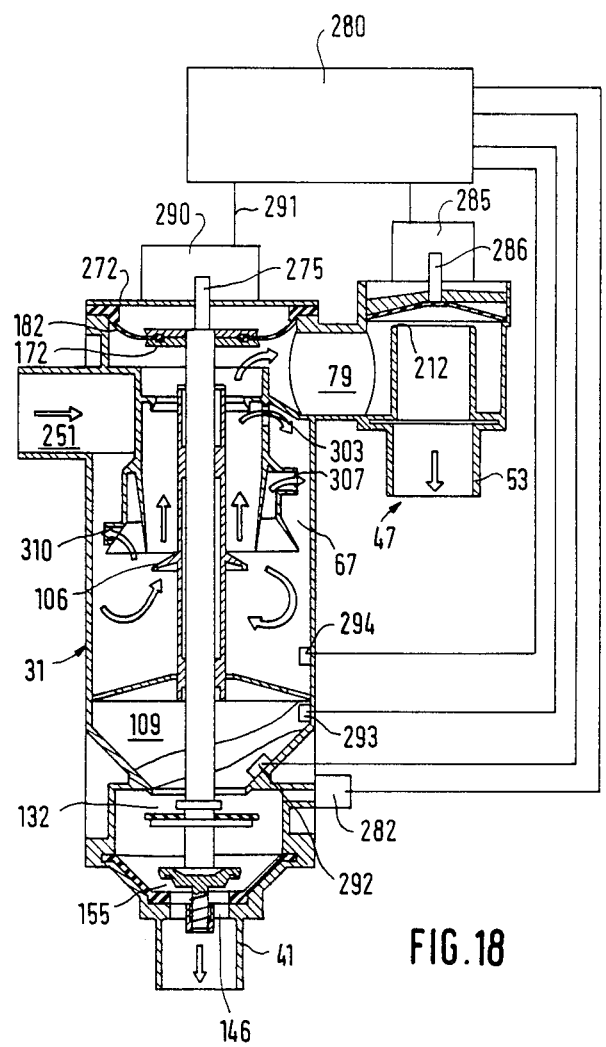
FIG. 18 is a representation, corresponding to FIG. 17, of a third embodiment of the invention.
Figure 19:
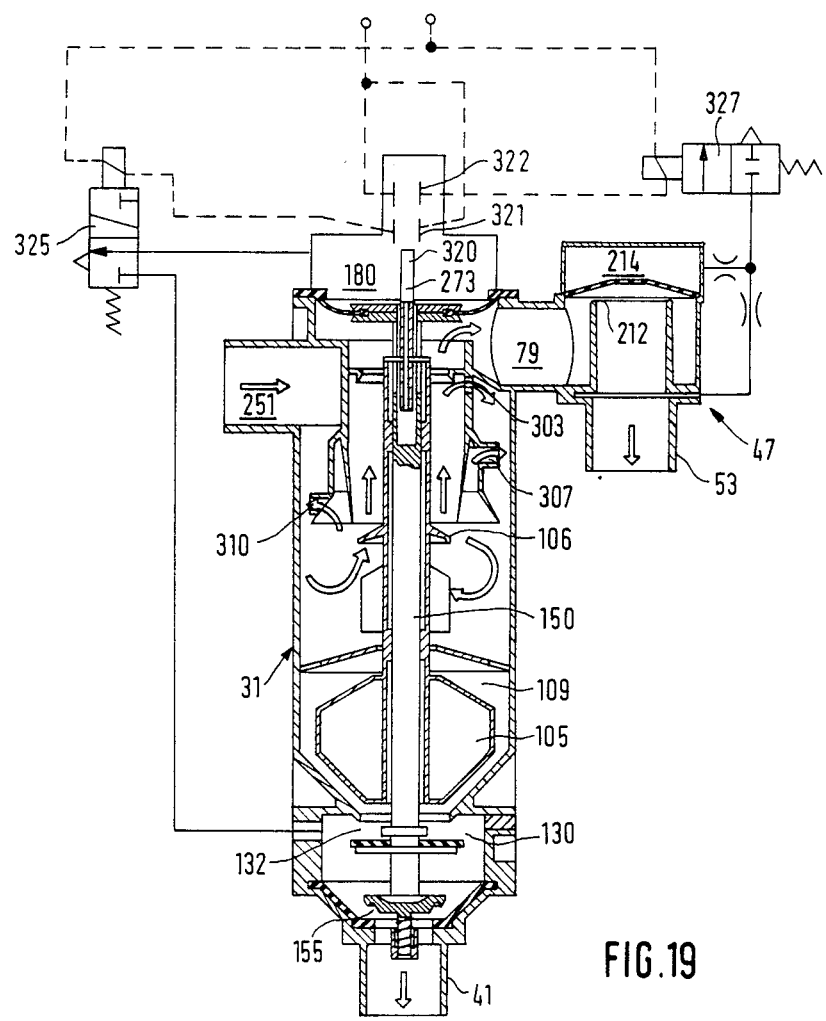
FIG. 19 is a representation, corresponding to FIGS. 17 and 18, of a fourth embodiment of the invention.

FIGS. 1–16 show a particularly advantageous embodiment of a small, high-efficiency, simple separator, which carries out all control functions with its own suction energy. The invention is however not limited to this particular embodiment, but can be varied in many ways. FIGS. 17–19 show some possible variations in respect of switching and the arrangement of the apparatus. The same and similar parts are provided with the same reference numerals as in FIGS. 1–16.

The separator of FIG. 17 is chiefly distinguished from the embodiment shown in FIGS. 1–16 in respect of its control function. The precipitation function is the same. However, the vanes 104 are in the precipitation chamber 72. Instead of the movable partition 172, at the top there is a fixed partition 272, through which there is guided a sleeve 273, which sits on the rotating pipe 105. The rod stem 150 is likewise guided by its upper end 275 in the interior of the sleeve 273 through the fixed partition 272. In a scanning and switching head 276, which is schematically represented as a box, three sensors 277, 278 and 279 are schematically represented. They detect the "full" position of the float 150 and emit through associated connections corresponding signals to a signal processing unit 280, which operates, in a manner not shown, on the upper end 275 and, through a connection 281, on an electromagnetic drainage chamber ventilation valve 282 in such a way that the functions, described above, of opening and closing of the valves 132 and 155 are carried out on sensing of the "full" positions of the float 115, whereby the ventilation valve 282, in conformity with requirements, allows atmospheric pressure to enter into the chamber 130 or shuts it off. The suction air shut-off valve 47 is closed by means of a control lead 287, with the aid of a schematically shown magnet 285, which operates on the valve rod 286, when necessary due to an external signal or if the sensor 279 is activated, when the chamber 109 is overfull. This embodiment shows that, with the same separation and precipitation stages, with the above-described movements of the air, moisture and solid material, the control can be effected with pick-up from the same sensor device and operation on the same valves either electromagnetically or in some other way.

In the embodiment of FIG. 18, the float is dispensed with. The rod 150 is operated by a valve operating mechanism schematically represented by a box 290, which is preferably electromagnetically operated, and which is connected by a lead 291 with a main control 280. In the secretion chamber 109, which has no float, there are provided a lower level sensor 292 and an upper level sensor 293, which sense the level of the liquid in known manner either electrically, electronically, or in some other way, and transmit their signals to the main control device 280 by means of the leads shown. The control device then feeds corresponding signals to the valve operating device 290, so that the outlet valves 132 and 155 are operated in the manner described above. An "over-full" signal emitter 294, on passing of the predetermined filling level, emits a signal to the control device 280, so that the electromagnet 285 closes the suction air shut-off valve 47. This embodiment shows that the float can be dispensed with and instead other sensor devices may be used to detect the presence of liquid in the secretion collection chamber. FIG. 19 shows another variation, in which the general arrangement is scarcely altered from that of the first embodiment. There are furthermore provided pneumatic control chambers for the control of the rod 150 and the suction air shut-off valve 47. Only the ancillary valves are represented as electromagnetic valves. The raising and lowering movement of the float 115 and of the rotating pipe 105 are sensed at the upper end 320 of a sleeve 273 with the aid of pick-ups 321 and 322. When the pick-up 321 is reached, the magnetic valve 325 switches off the entry of atmosphere to the chamber 130 and switches on the entry of atmosphere into the pneumatic control chamber 180, so that the rod stem 150 can descend. When the rotary pipe 105 descends, the magnetic valve 325 is again switched over. When an over-full position is reached, the pick-up 322 is operated and, through the magnetic valve 327, switches the suction air shut-off valve 47 into the closed position, so that protection against over-filling occurs in the above-described manner. These electromagnetic and pneumatic valves are to be connected in the manner commonly known to those skilled in the art. Otherwise, the device operates in the manner described above. Further mixed forms combined from elements of the variations described are also conceivable. If a large accumulation of secretion can be spatially accommodated, the drainage chamber 130 can be dispensed with and the separation can then be achieved with the cyclone insert shown but in more favourable manner. Instead of the separation with the aid of the cyclone insert, another mode may be selected, the receptacle being however so formed that only a small amount of secretion is collected and then released through a drainage chamber. In this connection it is important that by means of conduit devices, suitable choice of the shape of surfaces and the like, care should be taken that the secretion current does not come to rest and that the components cannot settle, so that the separator does not need to be opened by the dentist or his assistant for cleaning and disinfection.

What is claimed is:

1. A separator for incorporation in dental suction apparatus for processing a suction stream, composed of air and liquid and solid materials coming from the mouth of a patient to separate cleaned air from liquid and solid material, said separator comprising a housing, a separation chamber in said housing, an inlet for the suction stream into said separation chamber, an outlet opening for cleaned suction air from said separation chamber, means for continuously applying suction to said outlet opening, means in said separation chamber for separating air from liquid and solid materials of the incoming suction stream, a drainage chamber below said separation chamber, a discharge outlet for liquid-solid discharge from said drainage chamber, means for sensing liquid level in said separation chamber, first valve means between said separation chamber and said drainage chamber, second valve means between said drainage chamber and said discharge outlet and means for controlling said first and second valve means in coordination with one another to position said first valve normally closed and said second valve normally open during operation of said apparatus and to open said first valve and close said second valve when the liquid in said separation chamber reaches predetermined level to drain liquid and any solids therein from said separation chamber into said drainage chamber while suction continues to be applied to said outlet opening.

2. A separator according to claim 1, in which said means for separating said liquids and solids from said incoming suction current comprises an annular chamber in the uppermost part of said separation chamber, said inlet opening tangentially into said annular chamber and said annular chamber opening downwardly into said separation chamber.

3. A separator according to claim 2, in which said annular chamber has an inner wall defining a central passage into which suction air flows from said annular chamber, the flow of suction mixture in said annular chamber being circumferentially and downwardly and the flow of suction air in said central passage being upwardly.

4. A separator according to claim 1, in which said means for separating said liquids and solids from said incoming suction current comprises a rotatable member in said separation chamber, said member being rotated by said suction current.

5. A separator according to claim 4, in which said rotatable member comprises a float in a lower portion of said separation chamber and a stem extending up from said float, said float comprising said means for sensing liquid level in said separation chamber.

6. A separator according to claim 5, in which vanes on said stem in an upper portion of said separation chamber comprise means for rotating said float.

7. A separator according to claim 6, comprising in an upper portion of said separating chamber a cyclone insert having a generally cylindrical inner wall with a lower drip-edge, said vanes being above said drip-edge.

8. A separator according to claim 6, comprising a mushroom-shaped rejection surface on said stem between said vanes and said float.

9. A separator according to claim 5, comprising a conical partition in said separation chamber above said float with openings adjacent the periphery of said partition.

10. A separator according to claim 1, in which said means for sensing liquid level in said separation chamber comprises upper and lower electrical sensors, said first and second valve means being electromagnetically operated.

11. A separator according to claim 1, in which said means for sensing liquid level in said separation chamber comprises a float in said separation chamber and a stem extending up through an opening in the top of said separation chamber, comprising means for sensing the position of an upper portion of said stem and valve control means controlled by said sensing means.

12. A separator according to claim 1, further comprising means for shutting off suction on said separation chamber when the liquid level in said separation chamber rises above a predetermined level.

13. A separator according to claim 12, comprising means for delaying the turning on of suction on the separation chamber after the suction has been shut off, to permit draining of liquid and any solids therein from the separation chamber.

14. A separator for incorporation into dental suction apparatus for processing a suction stream composed of air and liquid and solid materials coming from the mouth of a patient to separate cleaned air from said liquid and solid materials, said separator comprising a housing, a separation chamber in an upper part of said housing, an inlet for the suction stream of air, liquid and solid materials into said separation chamber, means in said separation chamber for separating the air of said suction stream from said liquid and solid materials a cleaned air outlet in an upper part of said separation chamber, suction line means for continuously applying suction to said air outlet to draw cleaned air from said air outlet and thereby establish and maintain in said chamber a sub-atmospheric pressure to draw said suction stream into said separation chamber through said inlet, said separation chamber having a generally vertical cylindrical side wall and said separating means comprising a central sleeve extending down into said separation chamber from its upper end and defining an annular chamber between said sleeve and said side wall of said separation chamber, said sleeve being open at its lower end, said cleaned air outlet opening to said suction line being at the upper end of said sleeve and said inlet for the suction stream of air, liquid and solid materials opening approximately tangentially into said annular chamber above the lower end of said sleeve to induce a circular movement of said suction stream of air, liquid and solid materials around said sleeve before said air only flows into and up through said sleeve to said outlet opening, a collection region in a lower portion of said housing below said separating means to receive said liquid and solid materials separated from said suction stream by said separating means and falling into said collection region, a discharge opening at the bottom of said collection region for discharging liquid and solid materials, and means for automatically discharging liquid and solid materials from said collection region through said discharge opening while suction continues to be applied to air outlet by said suction line means to maintain said separation chamber under sub-atmospheric pressure, whereby liquid and solid materials are discharged without interruption of said suction stream drawn from the mouth of a patient.

15. A separator according to claim 14, in which said sleeve tapers downwardly.

16. A separator according to claim 14, in which there is at least one suction opening in said sleeve.

17. A separator according to claim 16, in which there are a plurality of said suction openings which are angularly offset with respect to each other.

18. A separator according to claim 16, in which said suction opening comprises a suction nozzle in the highest region of said annular chamber, said nozzle leading from said suction air outlet, and in which a restriction in said air outlet above said suction nozzle provides a rejection edge for trapping at least some of any liquid remaining in said suction air.

19. A separator according to claim 14 in which a further inner sleeve inside said sleeve defining said annular chamber defines a further concentric annular and slightly conical residual moisture chamber into which at least one said suction opening opens, lower edges of said sleeves constituting drip-edges for any liquid collected on said sleeves.

20. A separator according to claim 14, in which said sleeve has at its lower end an outwardly flared frustoconical skirt portion.

21. A separator according to claim 14, further comprising means for sensing the liquid level in said separation chamber and means controlled by said level sensing means to shut off suction applied to said separation chamber when the liquid level in said separation chamber rises above a predetermined level.

22. A separator according to claim 21, in which said liquid level sensing means comprises a float in said separation chamber having a stem extending up into said sleeve.

23. A separator according to claim 22, in which said means for shutting of suction comprises a valve in said suction line controlled by said float.

24. A separator for incorporation in dental suction apparatus for processing a suction stream composed of air and liquid and solid materials coming from the mouth of a patient, to separate cleaned air from liquid and solid material, said separator comprising a housing, upper and lower chambers one above another in said housing, a partition separating said upper and lower chambers, first valve means in said partition to afford communication between said chambers when said first valve means is open, second valve means in the bottom of said lower chamber to provide discharge therefrom when said second valve means is open, an inlet connected with a tube coming from the patient and opening into an upper portion of said upper chamber, a suction outlet opening into a upper portion of said upper chamber spaced from said inlet and connected with suction means for continuously drawing air from said upper chamber and thereby drawing a suction stream comprising air, liquid and solid materials into said upper chamber from said inlet, means for separating said liquid and solid materials from air, whereby said liquid and solid materials fall to the bottom of said upper chamber while cleaned air is drawn off through said suction outlet, and means for controlling said first and second valve means in coordination with one another to close said first valve means and open said second valve means whereby said upper chamber is under subatmospheric pressure, said lower chamber is at atmospheric pressure and said liquid and solid materials accumulate in said upper chamber, and alternately to open said first valve means and close said second valve means, whereupon said upper and lower chambers are both at the same subatmospheric pressure and said liquid and solid materials drain through said open first valve means from said upper chamber to said lower chamber.

25. A separator according to clam 24, in which said valve actuating means comprises means for sensing the liquid level in said upper chamber and actuating said valves to drain liquid and solid materials from said upper chamber when said liquid level reaches a predetermined level.

26. A separator according to claim 25, in which said liquid level sensing means comprises a float and said valve actuating means further comprises pilot valve means actuated by said float to actuate said fist and second valve means.

27. A separator according to claim 26, in which said first and second valves are actuated by fluid pressure.

28. A separator according to claim 25, further comprising means for shutting off suction from said suction means when said liquid level sensing means senses a second predetermined liquid level higher than said first mentioned liquid level.

29. A separator for incorporation into dental suction apparatus for processing a suction stream composed of air and liquid and solid materials coming from the mouth of a patient to separate cleaned air from liquid and solid materials, said separator comprising a housing, a separation chamber in an upper part of said housing, an inlet for the suction stream into said separation chamber, means in said chamber for separating the air of said suction stream from the liquid and solid materials, an air outlet in an upper part of said separation chamber, suction line means for continuously applying suction to said air outlet to draw cleaned air from said air outlet and thereby establish in said separation chamber a subatmospheric pressure to draw said suction stream into said separation chamber through said inlet, a collection region in a lower portion of said separation chamber below said separating chamber, a drainage chamber in said housing below said collection region and having a discharge outlet, first valve means between said drainage chamber and said collection region, second valve means controlling said discharge outlet of said drainage chamber, and means for controlling said first and second valve means in coordination with one another to close said liquid and solid materials to fall from said separation chamber into said drainage chamber, and alternately to open said second valve means and close said first valve means to segregate said drainage chamber from said collection region and separation chamber and to drain said liquid and solid materials from said drainage chamber while collecting liquid and solid materials in said collection region, whereby liquid and solid materials are discharged without interruption of said suction stream drawn from the mouth of a patient.

30. A separator according to claim 29, in which said separation chamber has at its lowest region a conical outflow surface terminating in a circular valve seat for said first valve means.

31. A separator according to claim 29, comprising a flexible diaphragm forming a lower wall of said drainage chamber, said diaphragm having a central opening surrounded by a rim which comprises a valve seat for said second valve means.

32. A separator according to claim 29, in which the volume of said drainage chamber is small in relation to said separation chamber.

33. A separator according to clam 29, in which said means for separating liquid and solids from the incoming suction current comprises a cyclone insert in an upper portion of said separation chamber, said insert comprising a generally cylindrical wall spaced inwardly from the wall of said separation chamber, a helical rib on said generally cylindrical wall and a flaring skirt at the lower end of said generally cylindrical wall.

34. A separator according to claim 33, comprising at least one suction nozzle in said generally cylindrical wall.

35. A separator according to claim 29, in which said first valve means comprises a valve seat, a support disk and an elastic sealing disk lying on and supported by said support disk and adapted to engage said valve seat.

36. A separator according to claim 35, in which said elastic sealing disk has at its periphery apertures the radially inner limits of which lie on a circle of slightly larger diameter than said valve seat.

37. A separator according to claim 29, comprising valve controlled means for venting said drainage chamber to the atmosphere when said first valve means is closed.

38. Apparatus according to claim 29, in which said means for controlling said first and second valve means comprises means for sensing the level of liquid and solid materials in said collection region, maintaining said first valve means closed and said second valve means open while the level of liquid and solid materials in said collection region is below a predetermined level, and opening said first valve means and closing said second valve means when the level of liquid and solid materials in said collection region rises to said predetermined level.

39. A method of processing a suction stream composed of air and liquid and solid materials coming from the mouth of a dental patient to separate liquid and solid materials from the air of said suction stream, which comprises drawing said suction stream through a separation chamber having an inlet for said suction stream, means in said chamber for separating liquid and solid materials from the air of said suction stream and an outlet for clean air freed of liquid and solid materials, by continuously applying suction to said clean air outlet to draw clean air out of said chamber through said clean air outlet and thereby create in said chamber a subatmospheric pressure to draw said suction stream into said chamber through said inlet, separating liquid and solid materials from air by means said separating means, whereupon said liquid and solid materials fall into a collection region below said separating means, providing below said collection region a drainage chamber having first valve means between said drainage chamber and said collection region and second valve means controlling a discharge outlet of said drainage chamber, operating said first and second valve means in coordination with one another to close said second valve means and open said first valve means to permit liquid and solid materials to fall from said collection region into said drainage chamber, and alternately to close said first valve means to segregate said drainage chamber from said collection region and separation chamber and open said second valve to drain said liquid and solid materials from said drainage chamber while collecting liquid and solid materials in said collection region, whereby liquid and solid materials are discharged without interruption of said suction stream drawn from the mouth of a patient.

40. A method according to claim 39, in which the cycle of operation of said first and second valve means is controlled by sensing the level of liquid and solid materials in said collection region, said first valve means being closed and said second valve means being open when the level of said liquid and solid materials in said collection region is below a predetermined level, and said first valve means being opened and said second valve means being closed when the level of said liquid and solid materials rises to said predetermined level.

* * * * *